(12) United States Patent
Tokonami et al.

(10) Patent No.: US 11,561,160 B2
(45) Date of Patent: Jan. 24, 2023

(54) COLLECTING DEVICE, COLLECTING KIT FOR MICROSCOPIC OBJECTS AND COLLECTING METHOD FOR MICROSCOPIC OBJECTS

(71) Applicant: University Public Corporation Osaka, Osaki (JP)

(72) Inventors: Shiho Tokonami, Sakai (JP); Takuya Iida, Sakai (JP); Kazushi Fujioka, Kobe (JP)

(73) Assignee: University Public Corporation Osaka, Osaki (JP)

( * ) Notice: Subject to any disclaimer, the term of this patent is extended or adjusted under 35 U.S.C. 154(b) by 962 days.

(21) Appl. No.: 16/301,310

(22) PCT Filed: May 11, 2017

(86) PCT No.: PCT/JP2017/017934
§ 371 (c)(1),
(2) Date: Aug. 8, 2019

(87) PCT Pub. No.: WO2017/195872
PCT Pub. Date: Nov. 16, 2017

(65) Prior Publication Data
US 2020/0182770 A1 Jun. 11, 2020

(30) Foreign Application Priority Data
May 11, 2016 (JP) .............................. JP2016-095494

(51) Int. Cl.
*G01N 15/08* (2006.01)
*B01L 3/00* (2006.01)
(Continued)

(52) U.S. Cl.
CPC ........ *G01N 15/08* (2013.01); *B01L 3/502761* (2013.01); *G01N 1/44* (2013.01);
(Continued)

(58) Field of Classification Search
CPC ............ G01N 15/08; G01N 1/44; G01N 1/04; G01N 1/2806; G01N 1/4022;
(Continued)

(56) References Cited

U.S. PATENT DOCUMENTS

2008/0023324 A1  1/2008 Ban et al.
2008/0305537 A1  12/2008 Sato et al.
(Continued)

FOREIGN PATENT DOCUMENTS

JP    2002-516742 A   6/2002
JP    2006-070254 A   3/2006
(Continued)

OTHER PUBLICATIONS

Karthaus et al., "Water-Assisted Formation of Micrometer-Size Honeycomb Patterns of Polymers," *Langmuir, the ACS Journal of Surfaces and Colloids*, American Chemical Society, vol. 16, No. 15 (Jul. 25, 2000).
(Continued)

*Primary Examiner* — Marrit Eyassu
(74) *Attorney, Agent, or Firm* — Marshall, Gerstein & Borun LLP

(57) ABSTRACT

The purpose of the present invention is to collect a plurality of microscopic objects dispersed in a liquid by light irradiation, and also trap them. A collecting device for bacteria collects a plurality of bacteria dispersed in a sample liquid. The collecting device is provided with a laser beam source that emits laser beam and a honeycomb polymer film constituted so as to be able to hold the liquid. Walls prescribing pores for trapping the plurality of bacteria dispersed in the liquid are formed on the honeycomb polymer film, and also a thin film that includes a material for converting light from the laser beam source to heat is formed on the honeycomb polymer film. The thin film heats the (Continued)

liquid of the sample through the conversion of the laser beam from the laser beam source to heat, thereby causing a convection in the liquid.

9 Claims, 21 Drawing Sheets

(51) Int. Cl.
  *G01N 1/44* (2006.01)
  *G02B 21/32* (2006.01)
  *G01N 1/04* (2006.01)
  *G01N 1/28* (2006.01)

(52) U.S. Cl.
  CPC .............. *G02B 21/32* (2013.01); *G01N 1/04* (2013.01); *G01N 1/2806* (2013.01)

(58) Field of Classification Search
  CPC ............ G01N 1/4077; G01N 15/1468; G01N 2001/4083; B01L 3/502761; B01L 2200/0668; B01L 3/50851; B01L 2200/12; B01L 2300/161; B01L 2300/1861; G02B 21/32; B25J 7/00; C12M 1/26; C12M 1/34; B01D 43/00
  USPC ............................................................ 73/38
  See application file for complete search history.

(56) References Cited

U.S. PATENT DOCUMENTS

| | | | |
|---|---|---|---|
| 2009/0134553 A1 | 5/2009 | Yamazaki et al. | |
| 2010/0261159 A1* | 10/2010 | Hess .................... | B01L 3/5025 435/7.1 |
| 2010/0290049 A1* | 11/2010 | Yang .................. | G01N 21/6458 977/773 |
| 2016/0069798 A1* | 3/2016 | Yokoyama ....... | G01N 33/54373 422/69 |
| 2017/0074760 A1* | 3/2017 | Iida ........................ | C12M 35/02 |

FOREIGN PATENT DOCUMENTS

| | | |
|---|---|---|
| JP | 2008-051803 A | 3/2008 |
| JP | 2009-103624 A | 5/2009 |
| JP | 2009-214044 A | 9/2009 |
| WO | WO-99/062622 A1 | 12/1999 |
| WO | WO-2006/126487 A1 | 11/2006 |
| WO | WO-2009/110237 A1 | 9/2009 |
| WO | WO-2015/170758 A1 | 11/2015 |
| WO | WO-2015170758 A1 * | 11/2015 .............. B01J 19/00 |

OTHER PUBLICATIONS

Feng et al., "Prediction of size effect on thermal conductivity of nanoscale metallic films," *Thin Solid Films* 517 (2009).

International Search Report issued in PCT Patent Application No. PCT/JP2017/017934 dated Jul. 4, 2017.

* cited by examiner

BEFORE CULTIVATION

AFTER CULTIVATION

COLLECTING DEVICE, COLLECTING KIT FOR MICROSCOPIC OBJECTS AND COLLECTING METHOD FOR MICROSCOPIC OBJECTS

TECHNICAL FIELD

The present invention relates to a collecting device for microscopic objects, to a collecting kit for use in collecting device, and to a collecting method for the microscopic object, more specifically, relates to a technology for collecting a plurality of microscopic objects dispersed in a liquid.

BACKGROUND OF THE DISCLOSURE

In recent years, technology for collecting microscopic objects at an aimed position has been proposed. For example, Japanese Unexamined Patent Publication No. JP 2009-214044 (PTD 1) discloses a method of separation of the first particles with a strong dielectrophoretic force by dielectrophoresis from a suspension containing the first particles and the second particles with weak dielectrophoretic force. In this separation method, by applying an AC voltage between electrodes provided on the substrate to form a non-uniform electric field, and the first and second particles are attracted in the vicinity of the electrodes by dielectrophoresis. By eliminating the second particle with weak dielectrophoretic force by generating localized flow near the electrodes from the vicinity of the electrodes, the first particles with strong dielectrophoretic force are collected in the vicinity of the area between the electrodes.

In the disclosed separation method in PTD 1, microscopic objects (particles in PTD 1) are collected by the voltage application between the electrodes. From the viewpoint of enlarging the scope of collecting techniques for microscopic objects, as a method other than an electrical method (applied voltage), optical methods (light irradiation) is desired.

Further, in the disclosed separation methods in PTD 1, once the microscopic objects are collected, in order to maintain (or trap) their positions in the vicinity of the region between electrodes, it is considered that a voltage must be continuously applied between the electrodes. It is desirable that the once collected microscopic objects be trapped more easily.

SUMMARY OF THE DISCLOSURE

The present invention has been made to solve the above problems, and the aim is collecting, and furthermore, capable of trapping a plurality of microscopic objects dispersed in a liquid by light irradiation.

A collecting device for microscopic objects according to an aspect of the present invention collects the plurality of microscopic objects dispersed in a liquid. The collecting device comprises a light source for emitting light, and a holding member which is capable of holding the liquid. In the holding member, an inner wall portion for defining a space in which a plurality of microscopic objects dispersed in the liquid are trapped is formed, and a Photothermal conversion area for converting light from the light source into heat is formed. Photothermal conversion area, by heating the liquid via converting light from the light source to heat, causes a convection in the liquid.

A collecting kit for microscopic objects according to another aspect of the present invention is used in the collecting device for collecting a plurality of microscopic objects dispersed in a liquid by light irradiation. The collecting kit comprises a support, and a holding member formed on the support and configured to be capable of holding the liquid. In the holding member, the photothermal conversion area including a material that converts light from a light source into heat is formed. Photothermal conversion area generates the heat for heating the liquid to cause a convection in the liquid by the light from the light source. The holding member has an inner wall portion for defining a space, in which a plurality of microscopic objects dispersed in the liquid are trapped.

Furthermore, a collecting method for microscopic objects according another aspect of the present invention collects a plurality of microscopic objects dispersed in a liquid. The collecting method comprises a step of providing a holding member. In the holding member, an inner wall portion for defining a space, in which a plurality of microscopic objects dispersed in the liquid are trapped, is formed, and a photothermal conversion area including a material which absorbs light and converts it into heat is formed. The collecting method further comprises a step of causing a convection in the liquid by irradiating light having a wavelength included in the light absorption band of the photothermal conversion member to the photothermal conversion area.

According to the present invention, a plurality of microscopic objects dispersed in a liquid are collected by light irradiation and furthermore, trapped.

DETAILED DESCRIPTION

Figure 1:
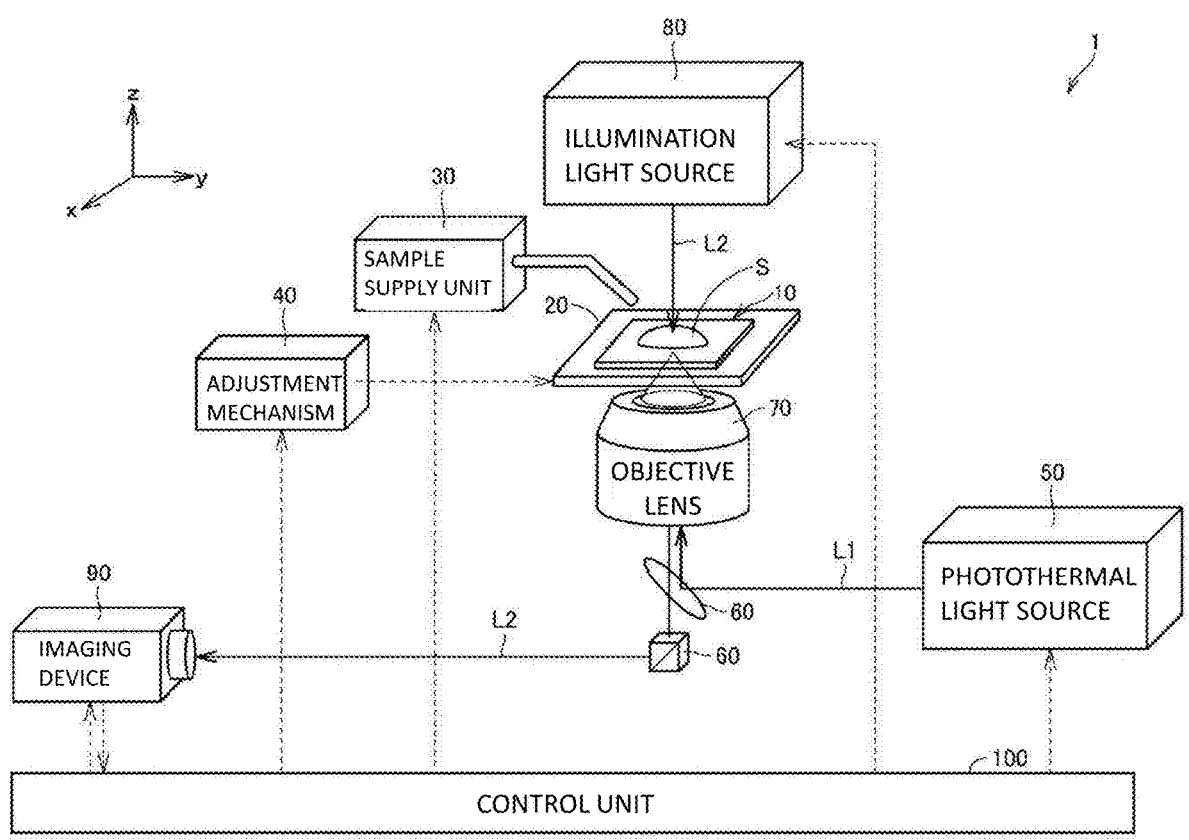
FIG. 1 shows a structure for the collecting device for bacteria according to the present embodiment is schematically shown.

Hereinafter, embodiments of the present invention will be described in detail with reference to the drawings. Incidentally, the description thereof is not repeated and the same reference numerals denote the same or corresponding portions in the drawings.

In the present invention and its implementation, the term "microscopic object" means an object having a size in the range from the order of nanometers to the order of micrometers. The shape of the microscopic object is not particularly limited, and is for example, spherical, oval sphere, rod type (rod-shaped). If microscopic object is elliptical sphere, at least one of the length along the minor axis and the length along the long axis of the oval sphere may be in the range from the order of nanometers to the order of micrometers. If microscopic object is rod-shaped, at least one of the width and length of the rod may be in a range from the order of nanometers to the order of micrometers.

Microscopic object may include an object derived from a living body. More specifically, microscopic objects can include, for example, cells, microorganisms (bacteria, fungi, etc.), an antigen (allergen or the like), viruses, and a biological material. "Biological material" may include proteins, nucleic acids, lipids, polysaccharides and similar biopolymers.

Other examples of microscopic objects include metal nanoparticles, the metal nanoparticles aggregate, metallic nanoparticle-assembled structure, semiconductor nanoparticles, organic nanoparticles, resin beads, PM (Particulate Matter), and the like. As specific examples of the PM, PM2.5, SPM (Suspended Particulate Matter) and the like may be referred to. The "metal nanoparticles" is a metal particle having a size on the order of nanometers. The "metal nanoparticle aggregate" is an aggregate of a plurality of metal nano-particles are formed by aggregation. The "metallic nanoparticle-assembled structure" is for example a structure in which a plurality of metallic nanoparticles are fixed on the surface of the beads through the interacting site, and spaced from each other by a distance less than or equal to the diameter of the metal nanoparticle. The "semiconductor nanoparticle" is a semiconductor particle having a size on the order of nanometers. "Organic nanoparticle" is a particle comprising an organic compound having a size on the order of nanometers. The "resin beads", are particles consisting of a resin having a size on the order of nanometers to that of micrometers. The "PM" is a particulate material having a size on the order of micrometers.

In the present invention and its implementation, "nanoorder" includes a range from 1 nm to 1000 nm (=1 μm). The "order of micrometers" includes a range from 1 μm to 1000 μm (=1 mm). Accordingly, the term "ranging from nanometer order to the order of micrometers" includes a range from 1 nm to 1000 μm. The term "range from nanometer order to the order of micrometers" typically represents several nm to several hundreds μm range and preferably indicates a range of 100 nm to 100 μm, more preferably 1 to several tens μm.

In the present invention and its implementation, the term "absorbs light" or "having a light-absorbing property" means the property that the intensity of light absorbed by the substance is greater than zero. Wavelength region of light may be any of any of ultraviolet region, the visible region and the near-infrared region, the region spanning the two regions of these three areas, and regions across all areas of the three regions. Light absorbing properties can be for example be defined by the scope of the absorption of light. In this case, the lower limit of the range of the absorption rate may be greater than zero, and it is not particularly limited. The upper limit of the range of absorption is 100%.

In the present invention and its implementation, the "honeycomb" is a shape formed of a plurality of regular hexagons 2-dimensionally in a hexagonal lattice shape (honeycomb shape). For each of the plurality of regular hexagons a pore is formed. The structure in which a plurality of pores are arranged in a honeycomb shape is referred to as a "honeycomb structure". Each pore is a hole having an opening ranging from the order of nanometers to the order of micrometers. Pores may be a non-through hole or may be a through hole. Also, the pore shape is not particularly limited, may include any shape excluding cylindrical, prismatic, spherical (e.g., hemispherical or semi-elliptical).

In the present invention and its implementation, the term "microbubble" is a bubble on the order of micrometers.

In the present invention and its implementation, the "interfacial tension" means the force for liquid to shrink the surface as much as possible at the solid-liquid interface, including capillary forces. The "capillary force" means the force by capillary phenomenon, i.e. a force for liquid to intrude in a gap between solid surfaces or a narrow space surrounded by a solid surface or a force to retain in the gap or space the liquid having intruded the gap or space. Incidentally, a capillary action is not limited to phenomena occurring in a capillary tube (or tubular structure), and may include phenomena occurring within the pores.

In the embodiments described below, bacteria are employed as an exemplary form of microscopic objects. However, the microscopic object as described above is not limited to bacteria.

Embodiment

<Configuration of the Bacterial Collecting Device>

FIG. 1 is a diagram schematically showing a configuration of a collecting device for bacteria according to the present embodiment. Collecting device 1 includes a collecting kit 10, an XYZ-axis stage 20, a sample supply unit 30, an adjusting mechanism 40, a laser beam source 50, an optical component 60, an objective lens 70, an illumination light source 80, an imaging device 90, and a control unit 100. Hereinafter, x and y directions represent the horizontal direction. The x and y directions are perpendicular to each other. z-direction represents a vertical direction. Direction of gravity is the z-direction downward.

Collecting kit 10 holds a sample S. In this embodiment, the sample S is a liquid in which bacteria B (see FIG. 2) are dispersed. The detailed configuration of the collecting kit 10 will be described in FIG. 3. Collecting kit 10 is mounted on the XYZ-axis stage 20.

Sample supply unit 30 follows the instruction from the control section 100 to supply liquid sample S on the collecting kit 10. The sample feed unit 30 can be, for example the dispenser.

Adjusting mechanism 40 follows the instruction from the control unit 100, to positionally adjust in x-, y- and z-directions the XYZ-axis stage 20 with the collecting kit 10 mounted thereon. Since in this embodiment the position of the objective lens 70 is fixed, by adjusting the position of the XYZ-axis stage 20, the relative positional relationship between the collecting kit 10 and the objective lens 70 is adjusted. As the adjusting mechanism 40, a driving mechanism such as a servomotor and a focusing handle that a microscope is equipped with can be used for example, although the specific configuration of the adjusting mechanism 40 is not particularly limited. The adjusting mechanism 40 may adjust the position of the objective lens 70 relative to the fixed collecting kit 10.

The laser beam source 50 follows the instruction from the control unit 100 to for example emit a near-infrared laser beam L1 (e.g. wavelength 1064 nm). However, the wavelength of the laser beam L1 is not limited thereto insofar as it is included in the optical absorption band of the material a thin film 13 indicated below (see FIG. 3).

The optical component 60 includes, for example a mirror, a dichroic mirror or a prism. The optical system of the collecting device 1 is adjusted so that the laser beam L1 from the laser beam source 50 is guided to the objective lens 70 by the optical component 60.

Objective lens 70 focuses the laser beam L1 from the laser beam source 50. Light focused by the objective lens 70 is irradiated to the collecting kit 10. Here, "irradiation" includes the case of the laser beam L1 passing through the collecting kit 10. That is, it is not limited to the case where the beam waist of the light focused by the objective lens 70 is located within the collecting kit 10. The optical component 60 and the objective lens 70 can be incorporated, for example in the inverted microscope main body or an erecting microscope body.

Illumination source 80 follows the instruction from the control unit 100 to emit white light L2 for illuminating the sample S in the collecting kit 10. As one example, it is possible to use a halogen lamp as the illumination light source 80. Objective lens 70 is also used to capture the white light L2 emitted to the collecting kit 10 from illumination source 80. White light L2 taken by the objective lens 70 is guided to the imaging device 90 by the optical component 60.

Imaging device 90 follows the instruction from the control unit 100 to capture an image of the sample S (see FIG. 2) in the collecting kit 10 irradiated with white light L2, and output the captured image to the control unit 100. For imaging device 90, a video camera comprising a CCD (Charge Coupled Device) image sensor or a CMOS (Complementary Metal Oxide Semiconductor) image sensor is used.

Control unit 100 controls sample supply unit 30, the adjusting mechanism 40, the laser beam source 50, illumination source 80 and imaging device 90. The control unit 100 performs predetermined image processing on the image taken by the imaging device 90. Control unit 100 is implemented by a microcomputer configured to include a CPU (Central Processing Unit), a memory, an input and output buffer and the like.

The optical system of the collecting device 1 is not limited to the configuration shown in FIG. 1, and may be configured to include an optical fiber or the like insofar as it can irradiate the collecting kit 10 with the laser beam L1 from the laser beam source 50 and also take the white light L2 from the collecting kit 10 into imaging device 90. Further, for the collecting device 1, the sample supply unit 30, the illumination light source 80 and the imaging device 90 are not essential components.

Figure 2:
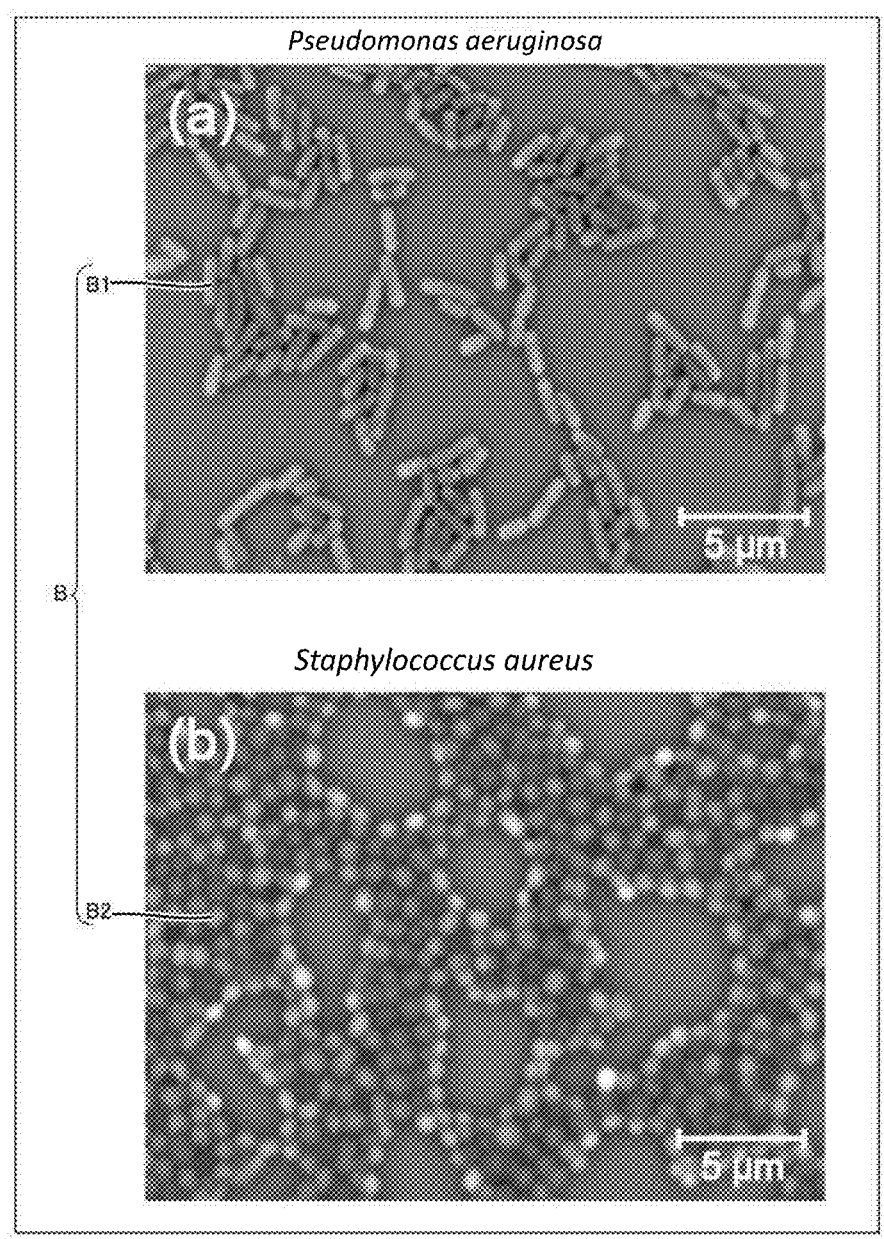
FIG. 2 is an image showing examples of bacteria included in the sample.

FIG. 2 is an image showing an example of bacteria B contained in the sample S. FIG. 2 (*a*) shows a SEM (Scanning Electron Microscope) image of a *P. aeruginosa*, in FIG. 2 (*b*) shows a SEM image of *Staphylococcus aureus*.

As shown in FIG. 2 (*a*), *P. aeruginosa* B1 is bacilli. The length of the major axis (longer diameter) of a typical *P. aeruginosa* (in this embodiment, NBRC (NITE Biological Resource Center) number 3080) is approximately 2 μm, and the length of its minor axis (shorter diameter) is approximately 0.5 μm. *P. aeruginosa* B1 is a gram-negative bacteria.

On the other hand, as shown in FIG. 2 (*b*), *S. aureus* B2 is cocci. The diameter of a typical *S. aureus* (NBRC number 102135 in the present embodiment) is about 0.8 μm. *S. aureus* B2 is a Gram-positive bacteria. In the following, when *P. aeruginosa* B1 and *S. aureus* B2 are not distinguished, they are described as bacteria B.

Figure 3:
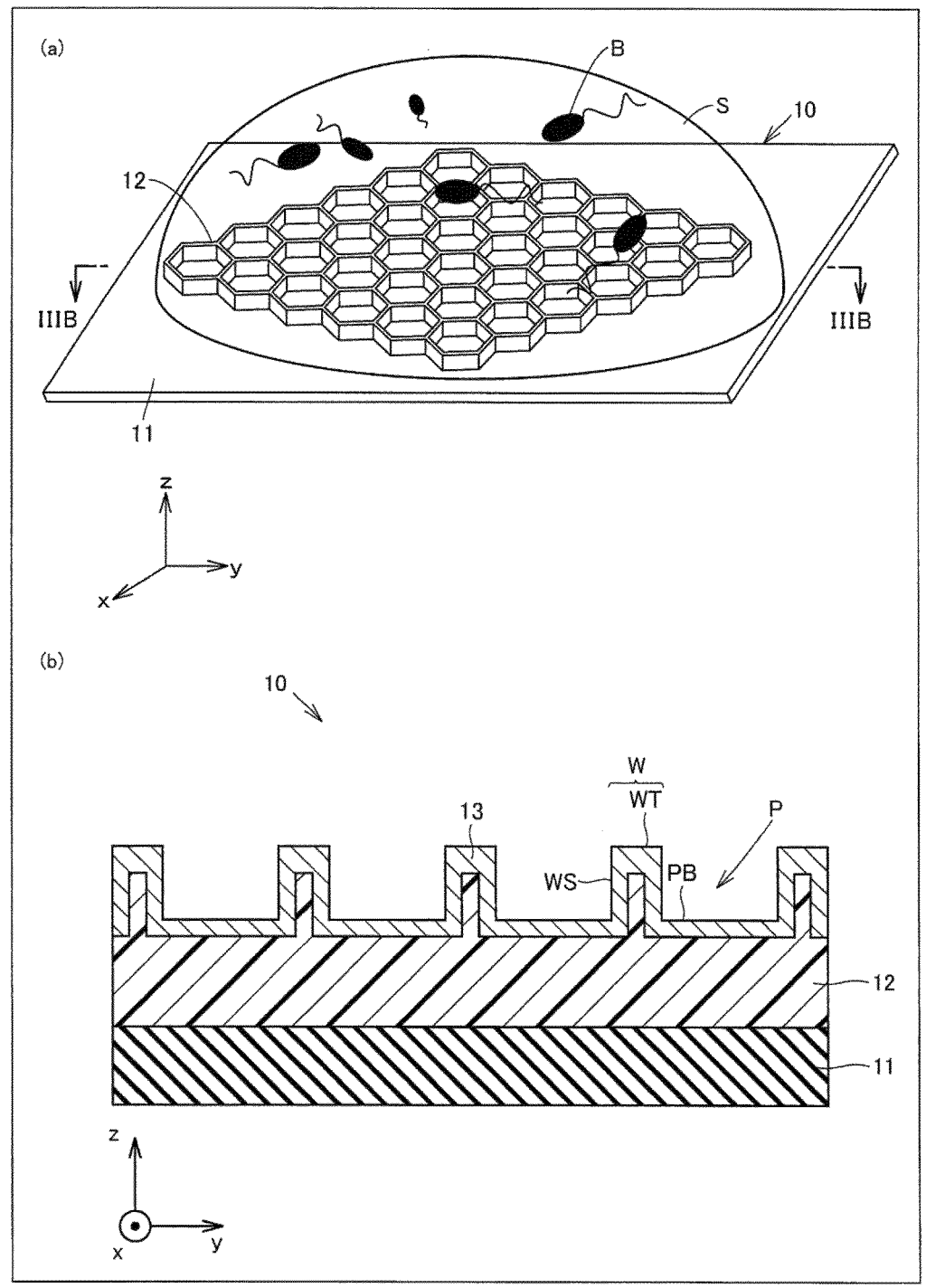
FIG. 3 is a conceptual diagram illustrating the configuration of a collecting kit.

FIG. 3 is a conceptual diagram for explaining the structure of the collecting kit 10. Referring to FIG. 3 (*a*), the collecting kit 10 includes a substrate 11, a polymer film in which a honeycomb structure is formed (hereinafter referred to as "honeycomb polymer film") 12, and a thin film 13.

The substrate 11 is for example a cover glass. Honeycomb polymer film 12 is formed on the substrate 11. Honeycomb polymer film 12 is a film in which a plurality of pores P are arranged in a honeycomb shape along its surface. The material of the honeycomb polymer film 12 may be a resin, and how it is manufactured with be described later. The substrate 11 corresponds to the "support" of the present invention. Honeycomb polymer film 12 corresponds to the "holding member" according to the present invention.

FIG. 3 (*b*) is a diagram for explaining a cross section of the collecting kit 10 along the line IIIB-IIIB of FIG. 3 (*a*). As shown in FIG. 3 (*b*), on the honeycomb polymer film 12 is a thin film 13 is further formed. While thin film 13 may be partially formed at a position the laser beam L1 is irradiated (a laser spot position), thin film 13 is formed so as to cover the entire surface of the honeycomb polymer film 12 in this embodiment that. Accordingly, the thin film 13 has a honeycomb structure reflecting the structure of the honeycomb polymer film 12. That is, in the thin film 13, a plurality of pores P arranged in a honeycomb shape (space) P is formed, and a partition wall W is formed to separate adjacent pores of the plurality of pores P. The bottom surface of the pore P is indicated by the PB. Further, a top of the partition walls W is indicated by WT, and a wall of the partition wall W (a side surface of the pore P) is indicated by WS. Side WS of the partition walls W corresponds to the "inner wall" of the present invention.

Thin film 13 absorbs the laser beam L1 from the laser beam source 50 and converts the light energy into heat. That is, thin film 13, (in other words, the top WT and side WS of the partition walls W and the bottom PB of pores PB) corresponds to the "photothermal conversion area" according to the present invention. Material of the thin film 13 is preferably a material having a property to highly absorb light of wavelength range of the laser beam L1 (in the present embodiment, near-infrared) (e.g. photothermal conversion efficiency). In this embodiment, gold thin film on the order of nanometers in thickness is formed as a thin film 13. Gold thin film can be formed by using a known technique such as sputtering or electroless plating. The thickness of the thin film 13 is preferably determined by design or experimentally considering the intensity of the laser beam L1, (hereinafter also referred to "laser power") and the light absorbing property of the material of the thin film 13. In the present embodiment, thin film 13 of 40 nm in thickness was formed by gold sputtering.

Preparation of the Honeycomb Polymer Hereinafter will be described a manufacturing method for the honeycomb polymer film 12 in this embodiment. For details of this manufacturing method, reference can be made for example to Karthaus O., N. Maruyama, X. Cieren, M. Shimomura, H. Hasegawa, T. Hashimoto, "Water-Assisted Formation Of Micrometer-Size Honeycomb Patterns Of Polymers", Langmuir 16, 6072-6076 (2000).

Figure 4:
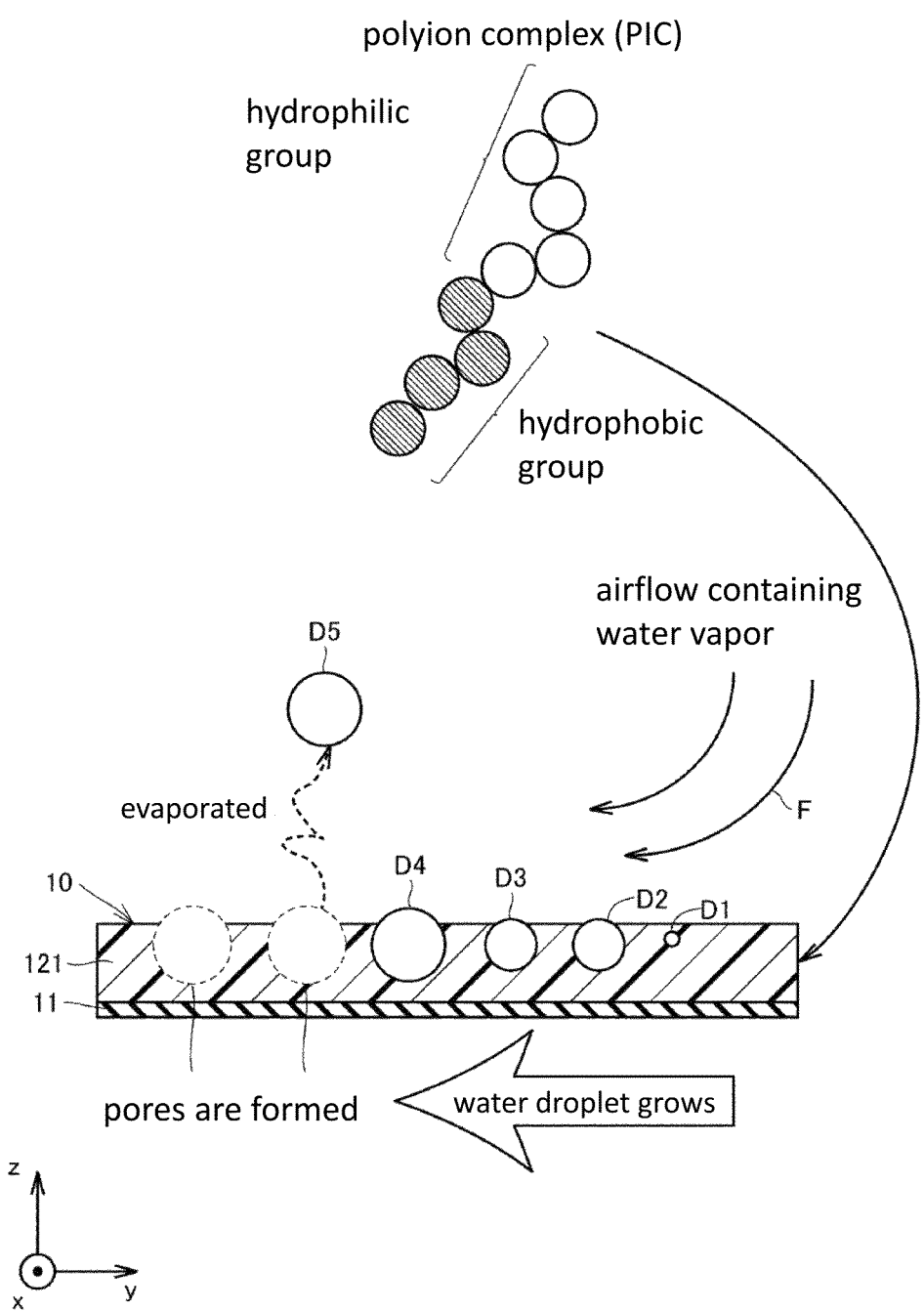
FIG. 4 is a conceptual diagram for illustrating a method of manufacturing a honeycomb polymer film.

FIG. 4 is a conceptual diagram for illustrating a manufacturing method for a honeycomb polymer film 12. For a substance of the honeycomb polymer film 12 (hereinafter referred to as "honeycomb substance"), it is possible to use a polymer soluble in an organic solvent (hydrophobic solvent). In this embodiment, polystyrene is used as the honeycomb substrate. To the honeycomb substrate, a trace amount of an amphiphilic polymer which has both hydrophilic and hydrophobic groups are added. In this embodiment, a polyion complex (PIC) having a dimethyl distearyl ammonium bromide as a hydrophilic group and Poly (styrenesulfonic acid) sodium salt as a hydrophobic group is added as an amphiphilic polymer. However, the type of amphiphilic polymer is not limited to PIC, and it may be a surfactant such as hexadecyltrimethylammonium bromide (CTAB).

Specifically will be described a solution preparation procedure for manufacturing a honeycomb polymer film 12. First, a solution in which 64.5 mg of sodium polystyrene sulfonate is dissolved in ultrapure water or 50 mL was stirred until it became transparent. Also, a solution in which 200 mg of dimethyl distearyl ammonium bromide was dissolved in 100 mL of ultrapure water is was stirred while being heated at 70 degree C. about to 80 degree C. to be translucent.

Subsequently, while stirring the solution of dimethyl distearyl ammonium bromide, and maintaining its temperature, a solution of sodium polystyrene sulfonate was added to a solution of methyl distearyl ammonium bromide and stirred for an additional 20 minutes. This produced colloidal PIC precipitate, which was in turn subjected to suction filtration. Suction filtered PIC was dried in a vacuum desiccator. Thereafter, 25 mg of polystyrene and 2.5 mg of PIC were mixed into 10 mL of chloroform, and the mixture was agitated vigorously for 5 minutes. Such a prepared solution 121 (hereinafter also referred to "honeycomb solution") of 500 μL was dropped onto the substrate 11.

Next, will briefly be described the procedure for manufacturing a honeycomb polymer film 12 from the honeycomb solution 121. As latent heat is removed by evaporation of the solvent of the honeycomb solution 121 (chloroform), the surface of the honeycomb solution 121 is cooled. Therefore, when airflow containing water vapor F is passed above the honeycomb solution 121, the solution surface was condensed by a temperature difference between the honeycomb solution and airflow F, (as indicated by D1) and a plurality of water droplets nuclei are generated. Each water droplet grows over time (as indicated by D1 to D4). At this time, as the PIC is contained in the honeycomb solution 121, coalescence of a plurality of water droplets is suppressed and the size of each droplet of water is made uniform. Then, a plurality of water droplets are arranged in a honeycomb shape by self-organization. Evaporation of the solvent gradually concentrates the honeycomb substance (or polystyrene), and when the concentration of the honeycomb substance reaches saturation concentration (solubility), the honeycomb substance is precipitated. That is, a plurality of water droplets are fixed in the honeycomb shape. Then (or in parallel with the evaporation of the solvent), each water droplet is evaporated (as indicated by D5).

Thus, a plurality of water droplets which are arranged in a honeycomb shape by self-organization can be used as a template to prepare a honeycomb polymer film 12. Since the magnitude of the electrostatic interaction with water molecules varies according to the type of amphiphilic polymer, and the growth degree of the water droplet is different. It is possible to adjust the pore size by using this property.

Figure 5:
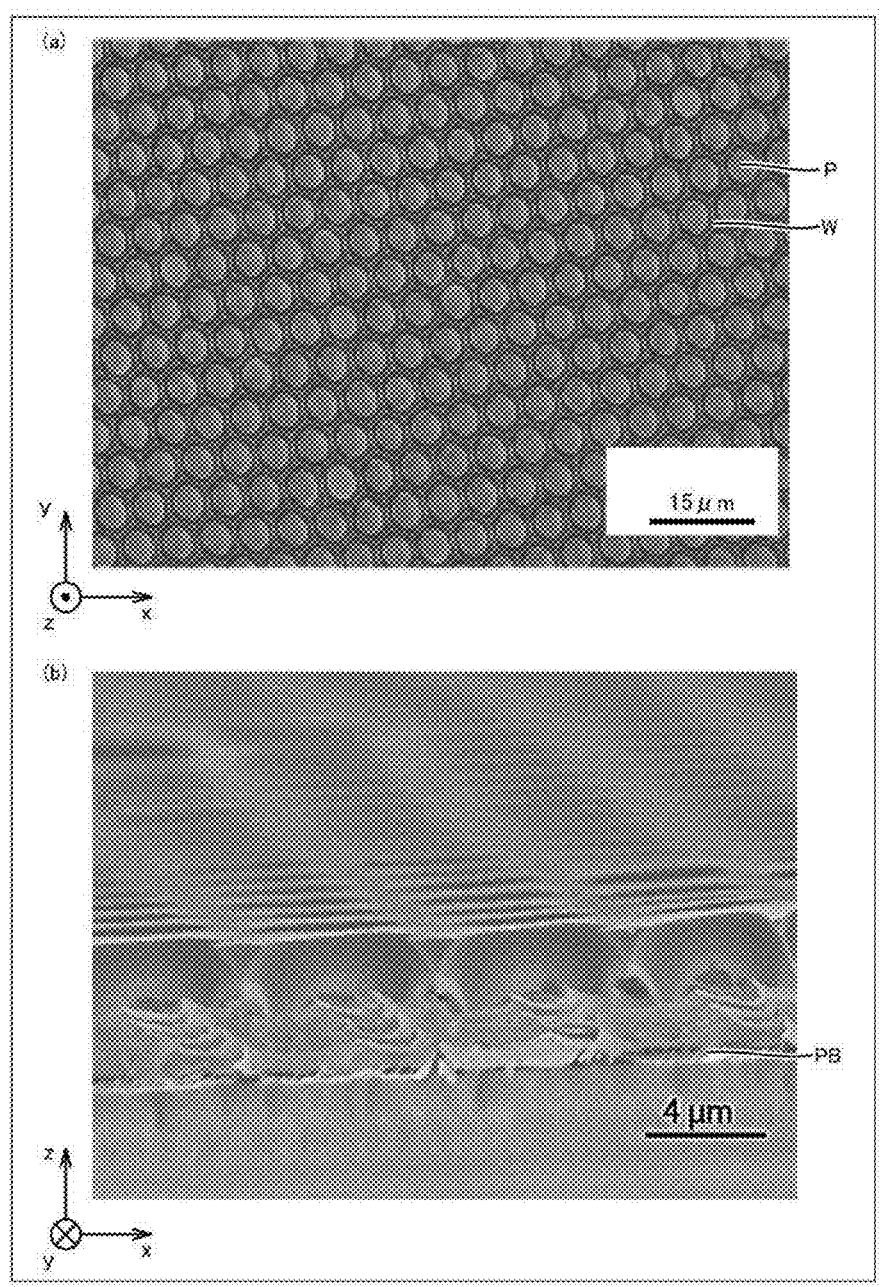
FIG. 5 is an image of a honeycomb polymer film fabricated in the present embodiment.

FIG. 5 is an image of a honeycomb polymer film 12 prepared in this embodiment. FIG. 5 (a) shows a top image of the honeycomb polymer film 12 (a stereoscopic microscope image). In FIG. 5 (a), a high regularity of the pores P of the honeycomb polymer film 12 is confirmed. More particularly, for the plurality of pores P, a diameter of pore openings along the xy plane direction (or pore size) was calculated to have an average pore diameter of approximately 5.0 μm. That is, the pore diameter is greater than the size (more specifically, the longer diameter) of bacteria B (P. aeruginosa B1 and S. aureus B2 shown in FIG. 2), and it can be seen that bacteria B can pass through the pores opening. Furthermore, the pore size had a standard deviation of 0.1 μm or less. This indicates that the pore size is highly uniform.

FIG. 5 (b) shows a cross-sectional image of the honeycomb polymer film 12 (SEM image). Diameter of the pores P (the diameter in xy plane direction of the pores P as viewed as spheres) is approximately 5.0 μm, the depth of the pores P was about 3.0 μm. That is, the depth of the pores P (or height of the partition wall W) is greater than the size of bacteria B (more specifically, short diameter of P. aeruginosa B1 and and diameter of S. aureus B2 shown in FIG. 2), and it can be seen that it is possible to trap bacteria B. Further, when observing the honeycomb substance that remains on the bottom PB of the pores P in detail, it can be seen that adjacent pores P are in communication with each other at the bottom side.

<Thin Film Formation>

Next, the results will be described of elemental analysis of gold-sputtered honeycomb polymer film 12 using an X-ray element analyzer.

Figure 6:
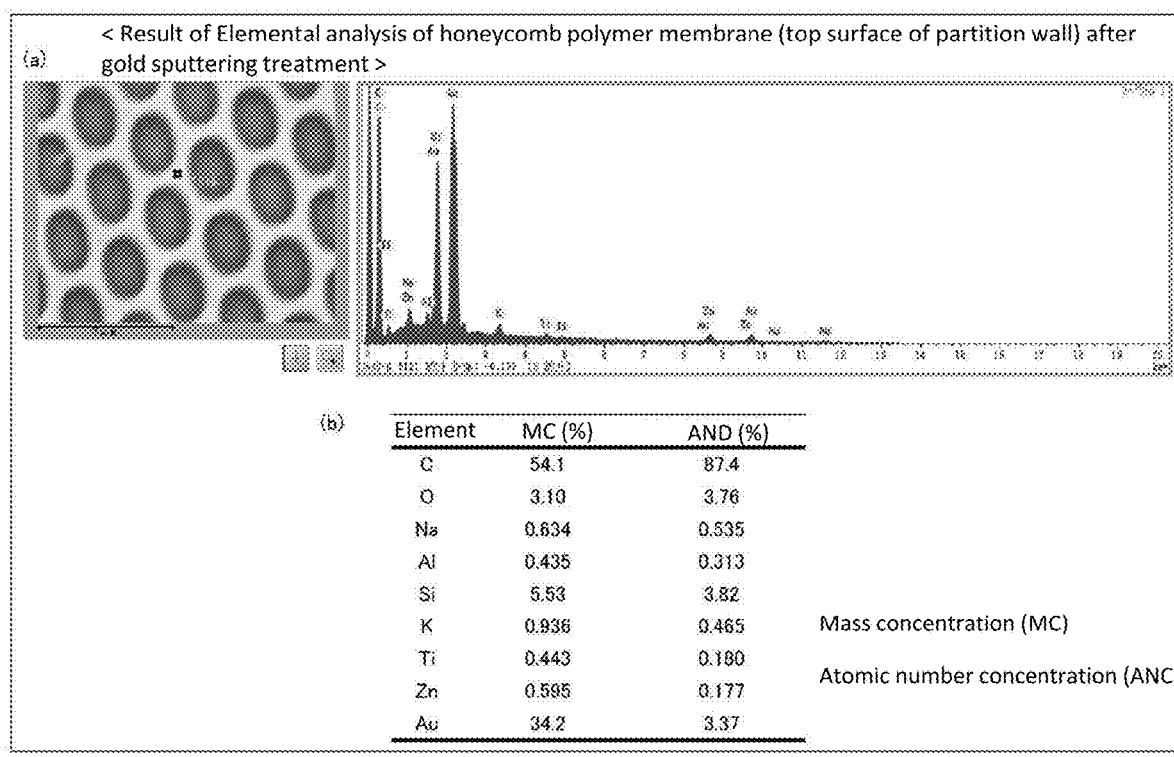
FIG. 6 is a diagram showing the results of elemental analysis of the top surface of partition wall of a honeycomb polymer film after gold sputtering.
Figure 7:
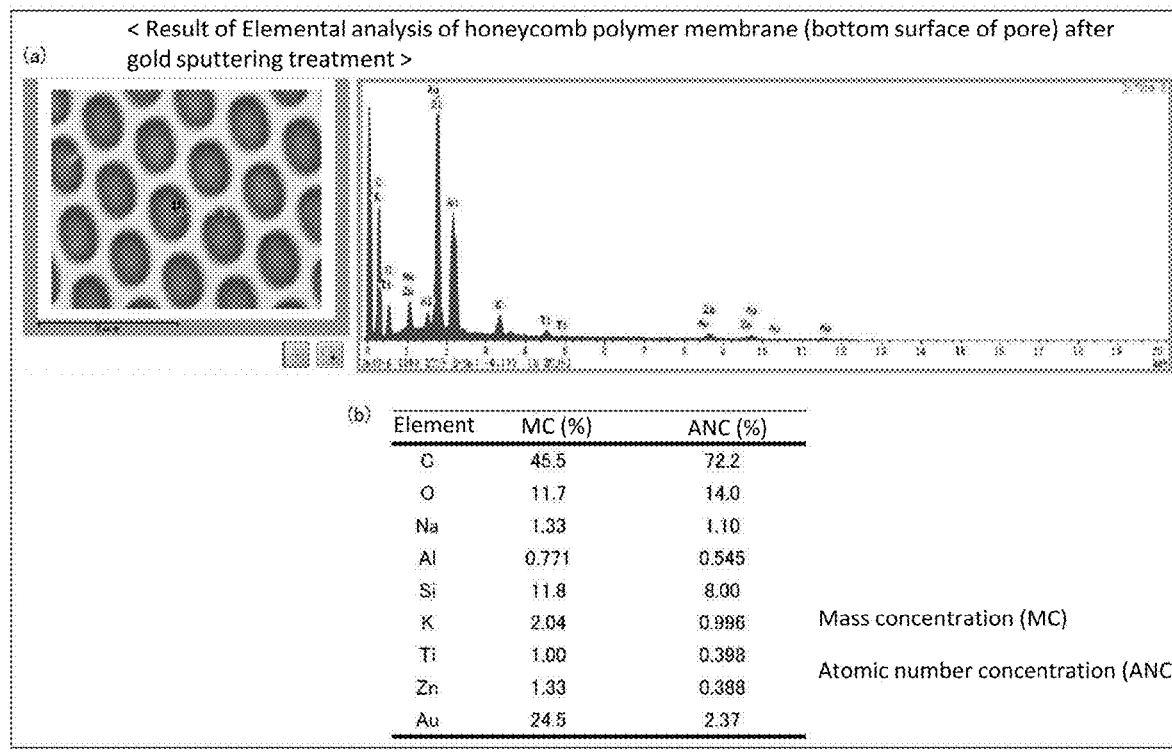
FIG. 7 shows results of elemental analysis of the bottom surface of pore of a honeycomb polymer film after gold sputtering.
Figure 8:
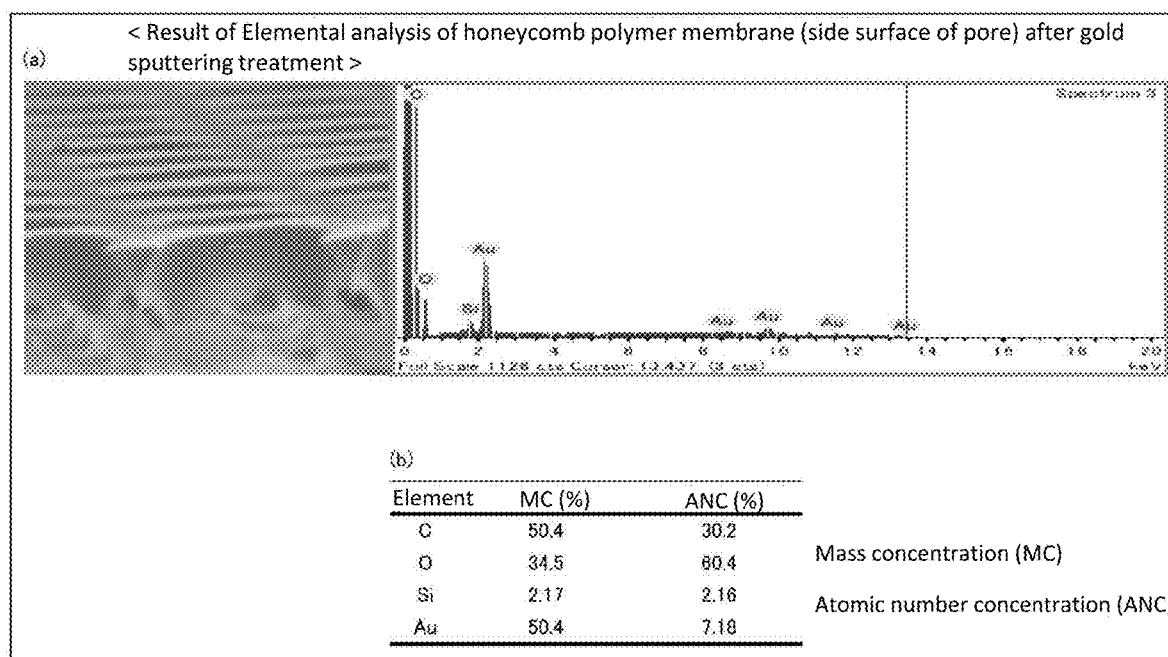
FIG. 8 is a diagram showing the results of elemental analysis of the side face of partition wall (pore wall surface) of a honeycomb polymer film after gold sputtering.

FIG. 6 is a diagram showing the results of elemental analysis of the top surface WT of the partition wall W of the honeycomb polymer film 12 after gold sputtering. FIG. 7 is a diagram showing the results of elemental analysis of the bottom PB of the pores P of the honeycomb polymer film 12 after gold sputtering. FIG. 8 is a diagram showing the results of elemental analysis of the side WS of the partition wall W of the honeycomb polymer film 12 after gold sputtering (walls of the pores P). Referring to FIGS. 3 (b) and 6 to 8, the peak derived from gold atoms were observed in the results of elemental analysis of all points. This has confirmed that the gold thin film is formed not only on the top surface WT of the partition wall W but also on the bottom PB and the wall surface of the pores P (side WS of the partition walls W).

In collecting kit 10 constructed as described above, liquid sample S in which bacteria B is dispersed is dropped on the thin film 13. In this embodiment, the liquid of sample S (a dispersion medium) is water (ultrapure water). Bacteria B may move in the sample S. For example, P. aeruginosa B1 has flagella and thus exhibits chemotaxis. In this embodiment the following method is employed to collect and furthermore, trap the bacteria B.

<Flowchart of Collecting Bacteria>

Figure 9:
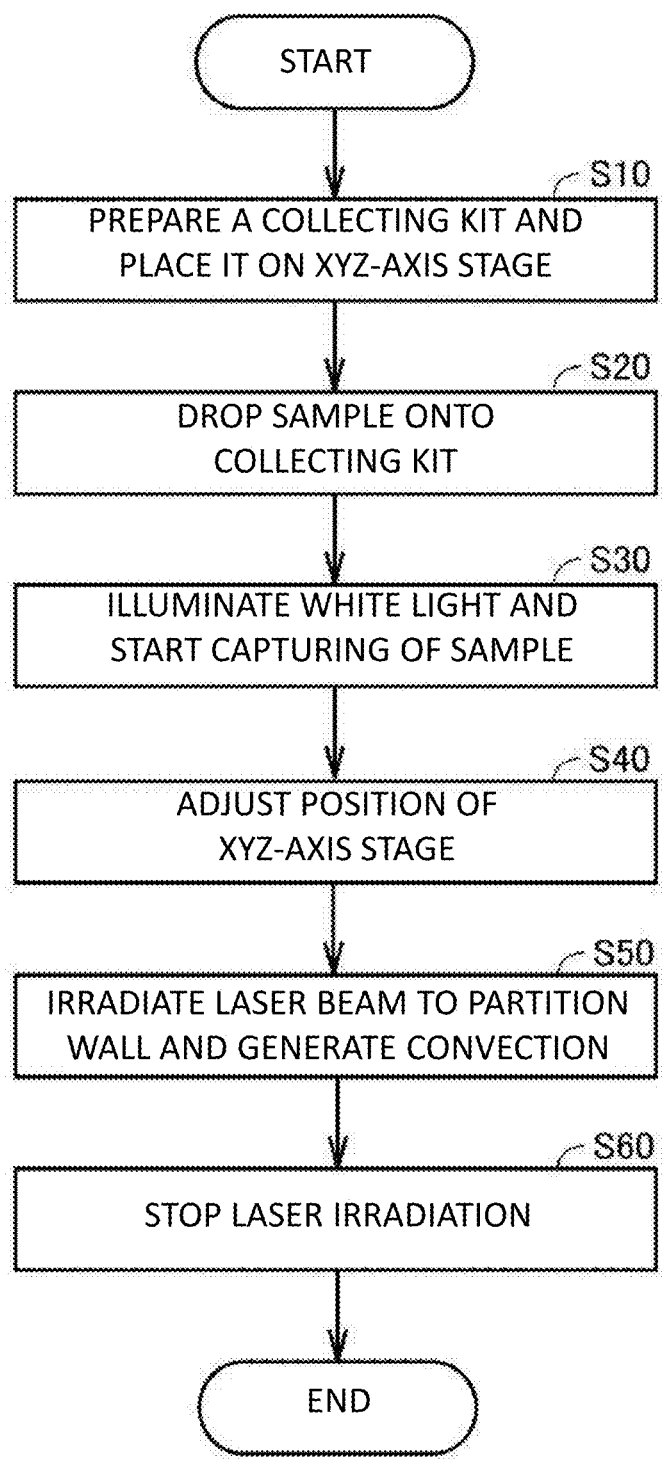
FIG. 9 is a flowchart illustrating a collecting method for bacteria according to the present embodiment.

FIG. 9 is a flowchart showing a process of collecting bacteria B according to the present embodiment. While steps in this flow chart are basically realized by software processing by the control unit 100, they may be realized partially or entirely by hardware (an electric circuit) fabricated in the control unit 100. It is assumed that at the start of the flowchart, the sample S in which bacteria B are dispersed is placed in the sample supply unit 30.

With reference to FIGS. 1 and 9, in step S10, the control unit 100 prepares and place a collecting kit 10 on the XYZ-axis stage 20. This process is realized, for example by the feed mechanism of collecting kit 10 (not shown).

In step S20, the control unit 100 controls the sample supply section 30 so that the sample S is dropped onto the collecting kit 10. Amount of the sample S dropped, as described above, for example, may be a small amount of about 500 µL, or may be a higher amount.

In step S30, the control unit 100 controls the illumination light source 80 to emit white light L2 for irradiating a sample S on the collecting kit 10, and controls the imaging device 90 to start capturing an image of the sample S.

In step S40, the control unit 100 adjusts the position of the XYZ-axis stage 20 by controlling the adjusting mechanism 40 so that the laser beam L1 from the laser beam source 50 is irradiated to an appropriate position of the collecting kit 10. The "appropriate position", which will be described in detail later, is preferably that the position of the partition wall W (see FIG. 3 and FIG. 10 (b) described later). This positional adjustment can be achieved by extracting the pattern of the pores P from the image recorded by the imaging device 90, for example, using the image processing technique for pattern recognition.

In step S50, the control unit 100 controls the laser beam source 50 to emit laser beam L1. The laser beam L1 is focused by the objective lens 70, and the focused light is irradiated to the partition wall W. Thus, convection occurs in the liquid sample S, and the bacteria B dispersed in a liquid is collected in the vicinity of the laser spot, and trapped in the pores P of the honeycomb polymer film 12. The appearance and the mechanism of collecting and trapping bacteria B is described in detail in FIGS. 10 to 12.

In step S60, the control unit 100 controls the laser beam source 50 to stop the irradiation of the laser beam L1 to the collecting kit 10. As a result, a series of processing is completed.

The step S30 is a process for observing sample S, and is not an essential process for collecting (and trapping) the bacteria B. Thus, the bacteria B can be collected (and trapped) even when executing the flowchart without step S30.

<Mechanism of Collecting Bacteria>

The following describes the mechanism and results of collecting bacteria B in this embodiment. In a collecting device 1 for the bacteria B according to this embodiment, thin film 13 is exposed to the laser beam L1 from the laser beam source 50 to generate heat via photothermal conversion, thereby facilitating the collecting of bacteria B.

Figure 10:
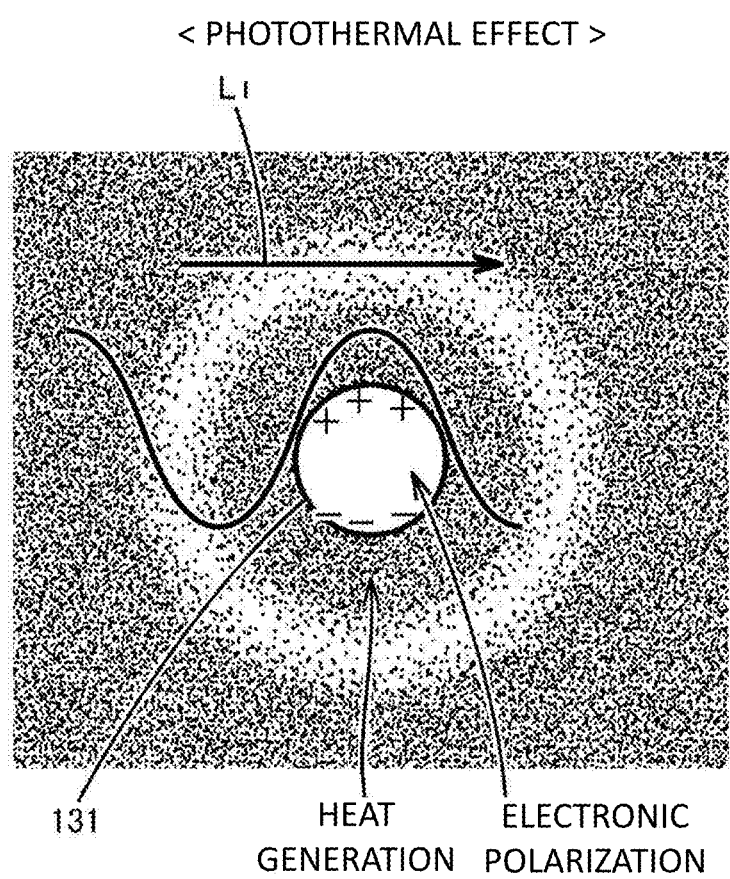
FIG. 10 is a diagram for explaining the principle of photothermal conversion.

FIG. 10 is a diagram for explaining the principle of photothermal conversion. As described in the FIG. 3 (b), on the honeycomb polymer film 12, a gold thin film having a thickness of nanometer order (40 nm in this embodiment) is formed as a thin film 13. The gold thin film, is generally is formed by gold sputtering resulting in fine irregularities on the order of nanometers, and it can be said that it is an assembled structure of gold nanoparticles 131 as shown in FIG. 10. Free electrons of the gold thin film surface form a surface plasmon and are vibrated by the laser beam L1. This causes polarization. The energy of the polarization is converted into the energy of the lattice vibration by the Coulomb interaction between the free electrons and atomic nuclei. As a result, the gold thin film generates heat. In the following, this effect is also referred to as "optical heating effects".

Incidentally, while in the present embodiment, a light having a wavelength of 1064 nm is used as the laser beam L1 to cause the photothermal effect, light of a wavelength close to the surface plasmon resonance wavelength of the gold thin film (a wavelength present in a visible light wavelength region of 400 nm to 800 nm in air or in water) may be used as the laser beam L1. Accordingly, even in the same laser power, it is possible to generate more heat.

Further, the material of the thin film 13 is not limited to gold, and may be metal elements other than gold that produce photothermal effect (e.g. silver) or metallic nanoparticle-assembled structure (for example, a structure using gold nanoparticles or silver nanoparticles), or the like. Alternatively, the material of the thin film 13, may be a material other than metal with high light absorptance in the wavelength band of the laser beam L1. Such materials include materials near the black body (such as carbon nanotube black body) and the like.

Figure 11:
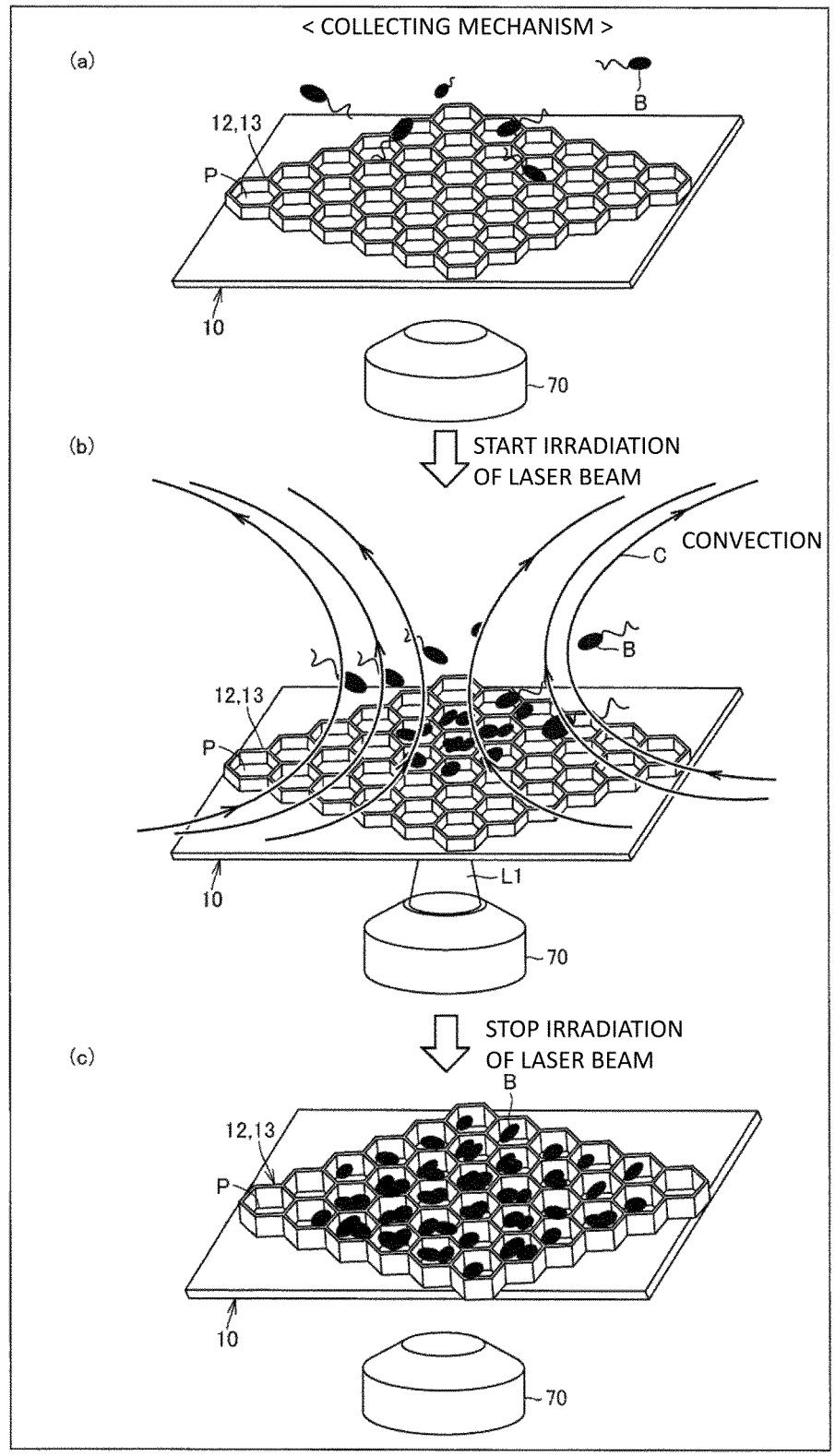
FIG. 11 is a diagram for explaining bacterial collecting mechanism in this embodiment schematically.

FIG. 11 is a diagram for explaining a bacterial collecting mechanism of the present embodiment schematically. In FIG. 11, to prevent the drawing from becoming complicated, the curve showing the interface of the liquid sample S is not shown.

As shown in FIG. 11 (a), before the start of irradiation of the laser beam L1 from the laser beam source 50, the bacterium B may move through the liquid of sample S freely. In pores P of the honeycomb polymer film 12 bacteria B is hardly caught.

However, when the irradiation of the laser beam L1 (hereinafter referred to as "light irradiation") is started, then, by the photothermal effect of the thin film 13 of the irradiation position of the laser beam L1 (a laser spot), the vicinity of the laser spot is heated locally. Thus, the liquid closer to the laser spot is higher in temperature. In other words, a temperature gradient occurs in the liquid by light irradiation. Due to this temperature gradient, regular thermal convection (or a laminar flow) is constantly generated in the liquid (see FIG. 11(b)). Hereinafter, the thermal convection is simply referred to as "convection". Direction of convection is, as shown by the arrow C, towards the laser spot is then away from the laser spot. The reason why convection occurs in a narrow region like this can be explained as follows. That is, liquid present in the vertical direction (z direction) above the heated area becomes relatively lean and elevated by buoyancy. At the same time, low-temperature liquid present in the heating area in the horizontal direction (xy direction) flows toward the heated region.

Bacteria B is conveyed toward the laser spot by the convection and thus collected in the vicinity of the laser spot. Here, the "collecting" means an effect by which the bacterium B is collected in the vicinity of the laser spot. When this is compared with the case where there is no light irradiation, the former allows bacteria B to more frequently (or more often per unit time) pass above pores P surrounding the laser spot. Bacteria B is trapped within the pores P when passing above the pore P. Here, the "trapping" refers to an effect by which the bacteria B are trapped in the space in the pores P. This trapping is considered to occur as follows. That is, when passing above the pores P in an area surrounding the laser spot (within a region of about 10 times the diameter of microbubbles MB) while being conveyed toward the laser spot, the bacteria B collide against the barrier wall W and drop in the liquid, and are thus trapped.

Thereafter, when the light irradiation is stopped, as shown in FIG. 11 (c), convection weakens. However, many of bacteria B trapped in the pores P is maintained in the trapped state. This collecting and trapping mechanisms will more specifically be described in comparison with a comparative example later (see FIGS. 20 and 21).

Thus, according to this embodiment, using the convection caused by photothermal effect by irradiating a laser beam L1 to the thin film 13 allows bacteria B to more frequently pass above the pores P surrounding the laser spot. This makes it possible to collect and trap the bacteria B, and it is possible to greatly reduce the time required for collecting and capturing bacteria B. Further, by using the honeycomb polymer film 12, bacteria B can be collected at a high density. Furthermore, it is possible to maintain a state in which the collected bacteria B are also trapped in the pores P after the light irradiation is stopped.

Figure 12:
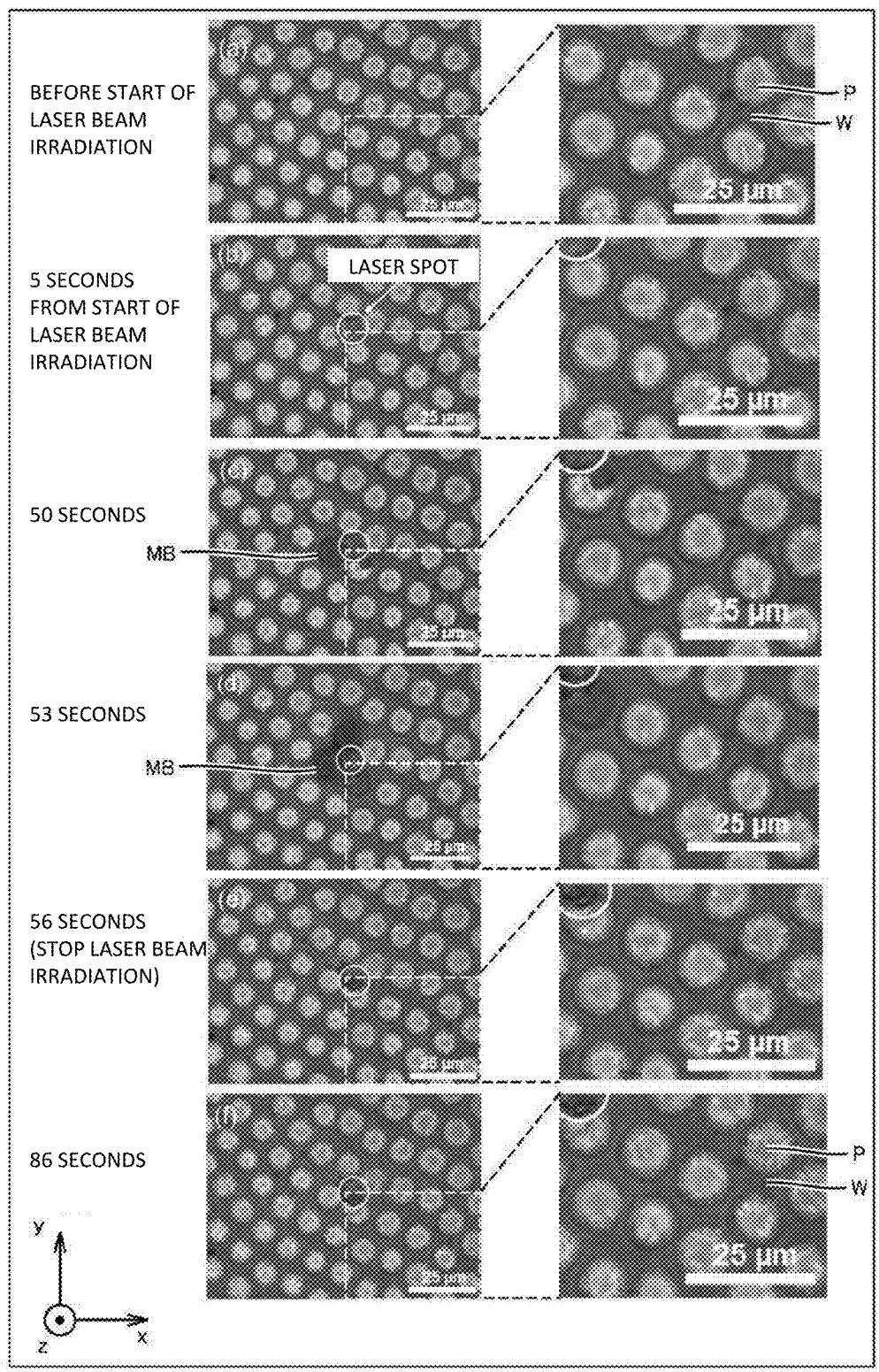
FIG. 12 is continuous images for explaining states of a honeycomb polymer film and behaviors of bacteria before and after the start of light irradiation.

FIG. 12 shows continuous images for explaining states of a honeycomb polymer film 12 and behaviors of bacteria B before and after the start of light irradiation. FIG. 12 (a) shows an image before starting the irradiation of the laser beam L1. FIG. 12 (b) to FIG. 12 (f) show images 5 seconds, 50 seconds, 53 seconds, 56 seconds, and 86 seconds, respectively, after light irradiation is started. Irradiation of the laser beam L1 is stopped 56 seconds after the light irradiation start.

Although some bacteria B (P. aeruginosa B1 in FIG. 12) are trapped in the pores P of honeycomb polymer film 12 before the light irradiation starts, they are trapped in a small amount (see FIG. 12 (a)).

Then, the light irradiation is started. FIG. 12 (b) to (d) show the laser spots by white circles, and it is understood that the laser beam L1 is irradiated on the top surface WT of the partition wall W (see FIG. 3 (b)). As shown in FIG. 12 (b), when the light irradiation is started, some bacteria B are collected in the vicinity of the laser spot, and trapped within the pores P. This is probably because a convection by light irradiation began.

Continuing the irradiation of the laser beam L1, as shown in FIG. 12 (c), how the vicinity of the laser spot becomes black was observed at the time of about 50 seconds after the light irradiation was started. This is probably because microbubble MB is generated due to the temperature rise of the vicinity of the laser spot liquid. Microbubbles MB grew with the passage of time (see FIG. 12 (d)). After microbubble MB is generated, a state was observed in which convection was caused around the laser spot. As a result, bacteria B is trapped not only the vicinity of the laser spot but also in the pores P even somewhat away from the laser spot. Also, how bacterium B trapped in the pores P moved was also observed.

When you stop the irradiation of the laser beam L1, as shown in FIG. 12 (e), microbubbles MB disappeared immediately. However, bacteria B once trapped in the pores P never escaped from the pores P although bacteria B continued to move in the pores P. Also, even in a state after 30 seconds from the light irradiation was stopped, bacteria were kept trapped in the pores P (see FIG. 12 (f)).

<Viability Test of Bacteria>

When the light irradiation excessively increases temperature of the liquid, collected bacteria B may be killed. Hereinafter will be described a result of determination of the viability of the collected bacteria B by fluorescence staining of the bacteria B.

Figure 13:
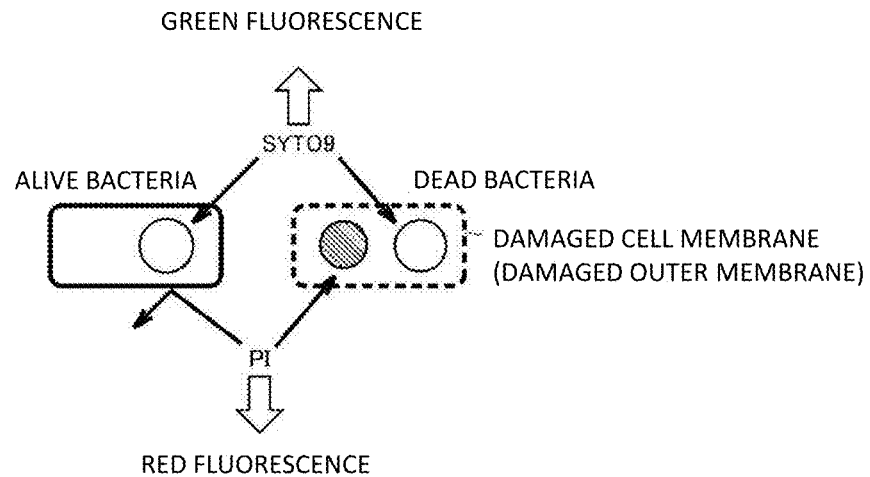
FIG. 13 is a diagram for explaining a fluorescent staining procedure for bacteria.

FIG. 13 is a diagram for explaining a fluorescent staining procedure for bacteria B. In this embodiment, SYTO 9 and (R) and PI (Propidium Iodide) are used as the fluorescent dye. SYTO9 is a DNA staining reagent with membrane permeability and stains DNA regardless of whether bacteria have cell membrane (outer membrane for P. aeruginosa, which is a Gram-negative bacteria) damaged. In other words, both the living bacteria (alive bacteria), and the dead bacteria with damaged cell membranes are stained with SYTO9. When the bacteria containing the SYTO9 are irradiated with light having an excitation wavelength of SYTO9 emits green fluorescence. Meanwhile, PI has no membrane permeability. Therefore, only the bacteria (i.e. killed) having damage to the cell membranes is stained with PI. Read fluorescence is emitted when PI is excited from the outside.

Figure 14:
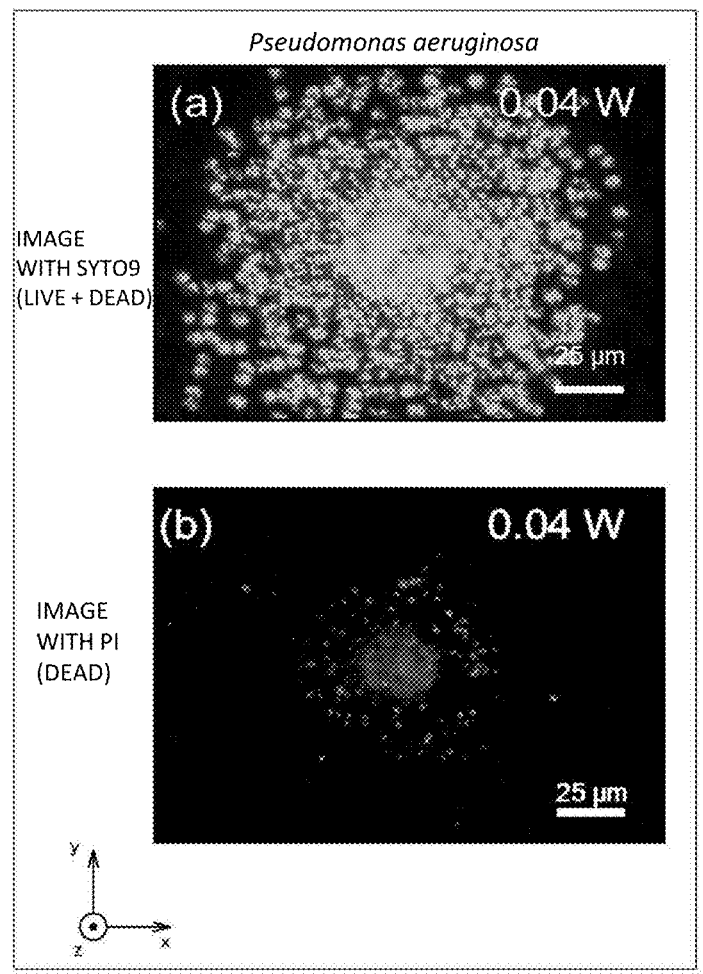
FIG. 14 shows fluorescent observation images of the collected *Pseudomonas aeruginosa* (*P. aeruginosa*).
Figure 15:
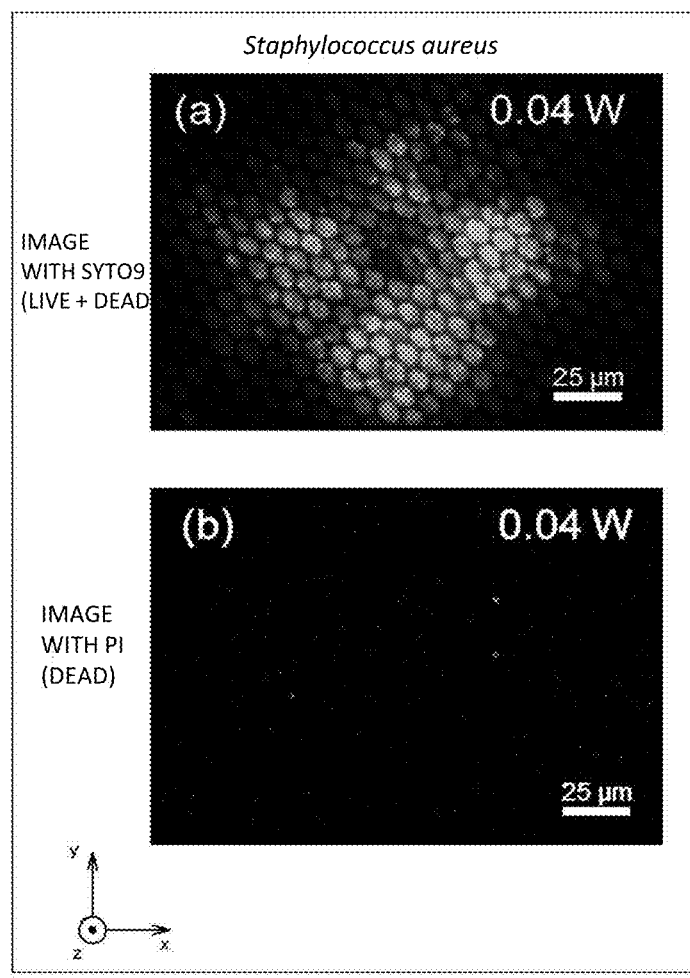
FIG. 15 shows fluorescent observation images of the collected *Staphylococcus aureus* (*S. aureus*).

FIG. 14 is a fluorescent observation image of the collected P. aeruginosa. FIG. 15 is a fluorescent observation image of the collected S. aureus. FIG. 14 (a) and FIG. 15(a) show the fluorescence observation images by the excitation wavelength of SYTO9 (hereinafter also referred to "SYTO9 image"). FIGS. 14 (b) and 15 (b) show the fluorescence observation images by the excitation wavelength of the PI (hereinafter also referred to "PI image"). The laser spot is located substantially at the center of each image. Laser power from the laser beam source 50 were 0.04 W for all images. Magnification of the objective lens is 100 times, the laser power after passing through the objective lens 70 was about 20% of the laser power from the laser beam source 50.

From SYTO9 image, it can be seen that, regardless of the type of bacteria, that is, whether bacteria B are bacterial species P. aeruginosa or Staphylococcus aureus, the bacteria can be collected around the laser spot at high density and trapped in the pores P As shown in PI image, dead cells are slightly observed in the vicinity of the laser spot for both P. aeruginosa and S. aureus. Moreover, comparing the SYTO9 image and PI image of the same species, the amount of bacteria (an amount of living cells+dead cells) observed in PI image is smaller than that observed in SYTO9 image, and a high survival rate of the bacteria B is suggested.

As the reason why the bacteria B trapped in the vicinity of the laser spot are killed, the vicinity of the laser spot is considered to become a high temperature locally, as described above. This is evidenced by the fact that the glass transition of the polystyrene that is a substrate of honeycomb polymer film 12 was observed near the laser spot as polystyrene has a glass transition point of approximately 100° C.

<Laser Power Dependence>

Next, a description will be given of a laser power dependency of collection density of bacteria B (or a density of the collected bacteria B) and viability condition of bacteria B.

Figure 16:
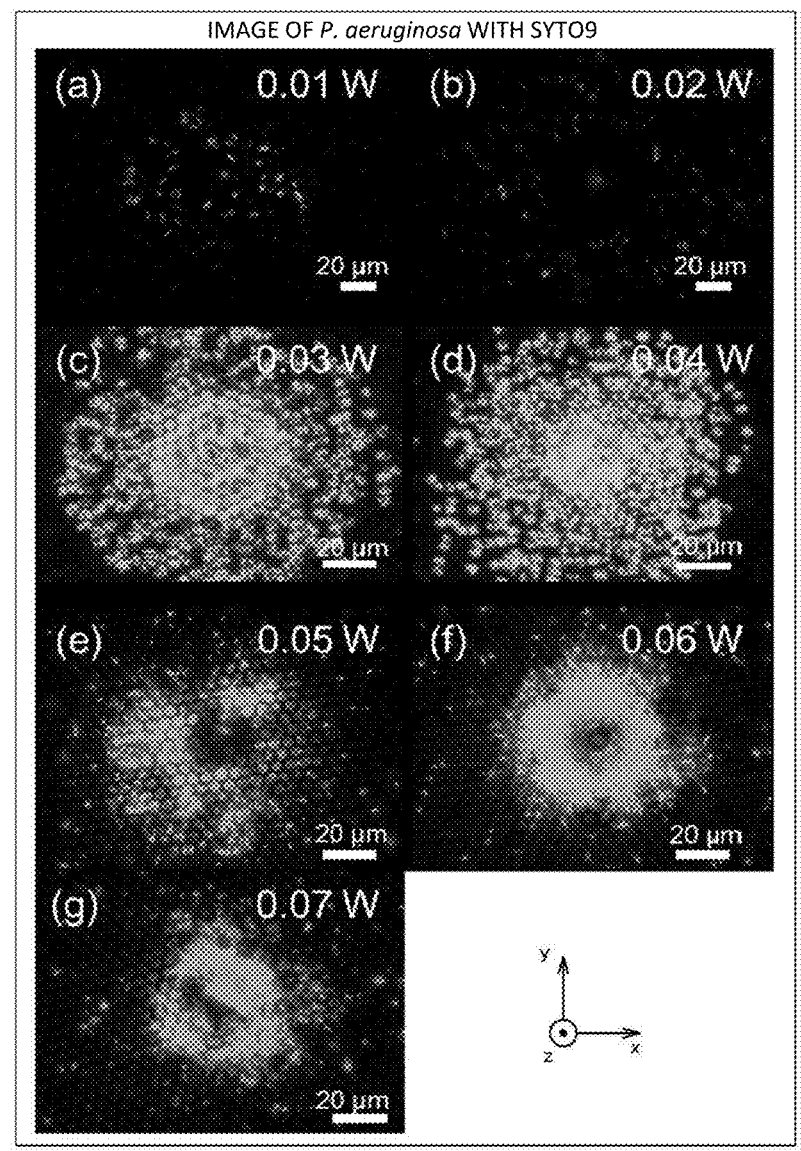
FIG. 16 shows fluorescent observation images to compare amounts of *P. aeruginosa* trapped in different laser power conditions.
Figure 17:
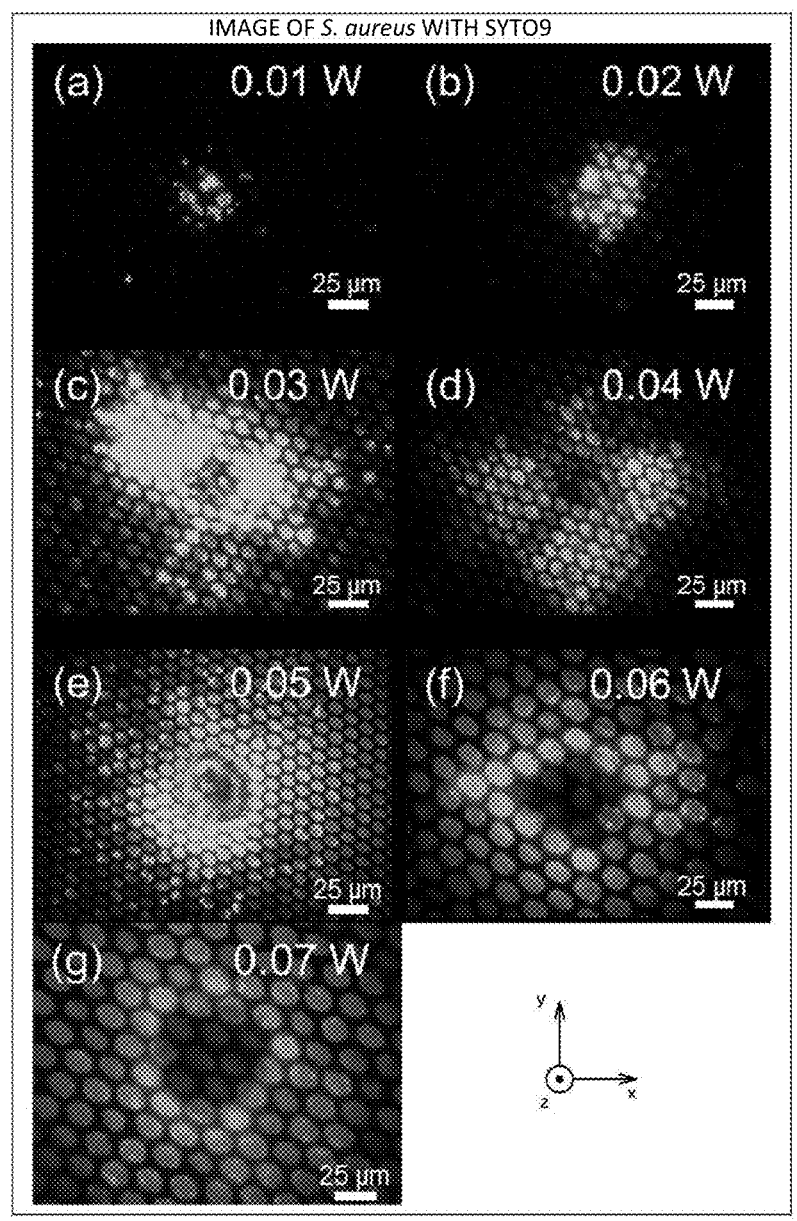
FIG. 17 shows fluorescent observation images to compare amounts of S. aureus trapped in different laser power conditions.

FIG. 16 is fluorescent observation images to compare amounts of the collected P. aeruginosa under different laser power conditions (SYTO9 images). FIG. 17 is fluorescent observation images to compare amounts of the collected Staphylococcus aureus under different laser power conditions (SYTO 9 images). FIG. 16 shows the results when the laser power from the laser beam source 50 varies by 0.01 W ranging from 0.01 W to 0.07 W. The same is true for FIG. 17. The laser spot is located substantially at the center of each image. Although not shown, PI image is also acquired in addition to the SYTO9 image.

As shown in FIGS. 16 and 17, *P. aeruginosa* and *S. aureus* both had more bacteria B trapped around the laser spot as the laser output increased.

Also, as particularly noticeably observed in FIG. 16 (*e*) to FIG. 16 (*g*) and in FIG. 17 (*e*) to FIG. 17 (*g*), even in the vicinity of the laser spot, there is an area in which bacteria B are not collected. This is presumably because bacteria B cannot enter a region immediately below microbubbles MB (a region between the microbubbles MB and the thin film 13), and as the laser power increases, microbubbles MB grow larger, which increases the area that the bacteria B cannot enter.

Bacteria stained by SYTO9 (living+dead) is observed as a green bright point under light irradiation of the excitation wavelength of SYTO9. Therefore, by counting green bright points observed in the observation area recorded by the COD camera, it is possible to obtain the number of collected bacteria (or total number of bacteria). It is possible to calculate the collection density of the bacteria B from the thus determined number of bacteria in accordance with the following equation (1).

$$\text{Collecting Density} = \text{number of green bright points} / \text{observation area} \quad (1)$$

Meanwhile, bacteria stained with PI (dead) is observed as a red luminescent spot under light irradiation of the excitation wavelength of PI. Like the SYTO9 image for H image as well, it is possible to determine the number of dead bacteria from the red bright points.

In this embodiment, the viability of the bacterium Bis defined by the following formula (2). That is, the difference between the total number of bacteria and the number of dead bacteria is estimated and a ratio of the number of living bacteria relative to the total number of bacteria was defined as a survival rate. Then, the survival rate was calculated by counting the green bright points and red bright points.

$$\text{Survival rate} = (\text{green bright points} - \text{red bright points}) / \text{green bright points} \quad (2)$$

Figure 18:
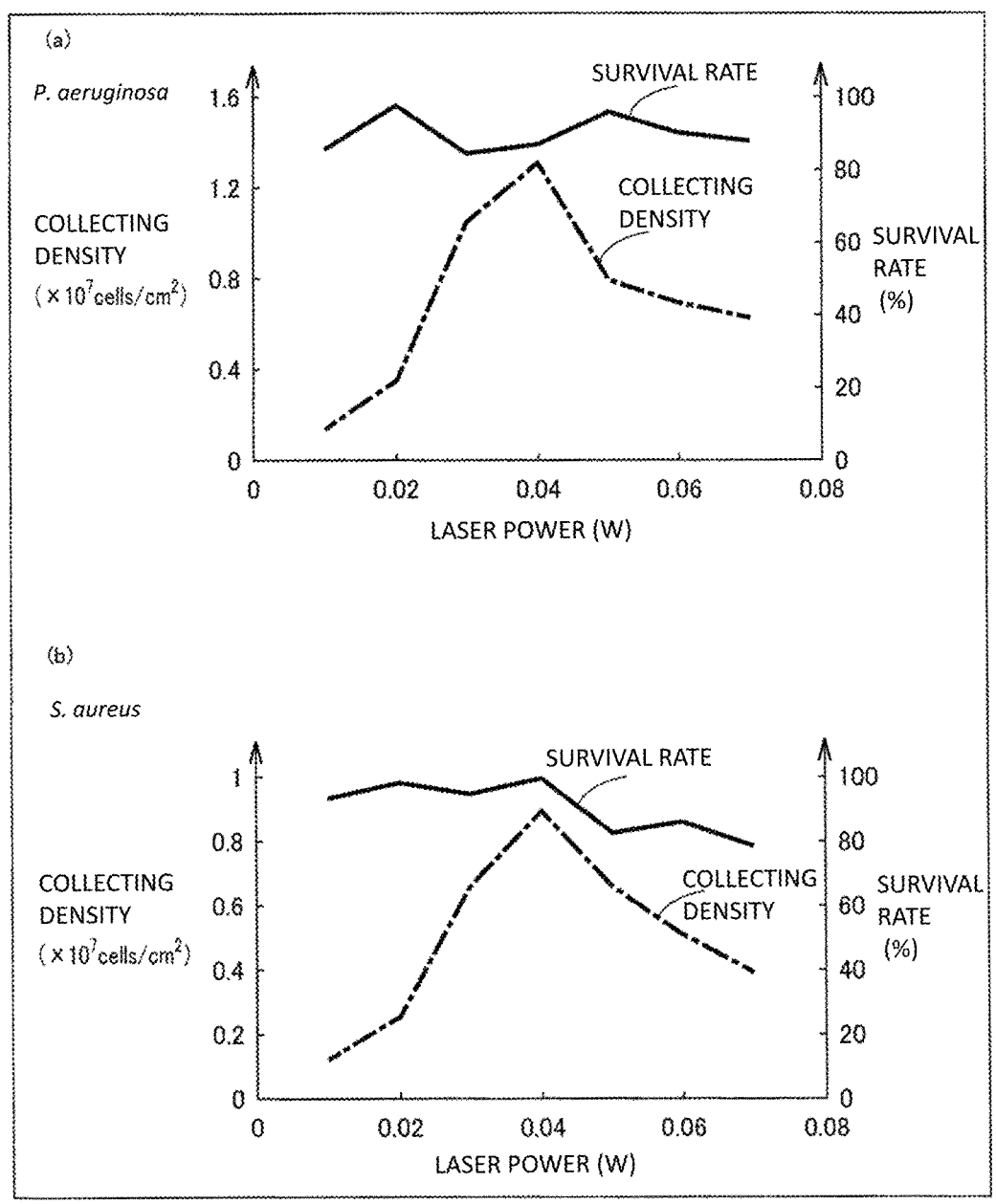
FIG. 18 shows diagrams indicating laser power dependence of collection density and viability of the bacteria.

FIG. 18 is a diagram showing a laser power dependency of collection density and survival rate of the bacterium B. FIG. 18 (*a*) shows the calculation results for *P. aeruginosa*, FIG. 18 (*b*) shows the calculation results tor *Staphylococcus aureus*. In FIG. 18 (*a*) and (*b*), the horizontal axis represents the laser power from the laser beam source 50. The left vertical axis represents collection density of bacteria B [Unit: $10^7$ Cells/cm$^2$] and the right vertical axis represents the survival rate of the bacteria B.

Viability survival rate was found for both the *P. aeruginosa* and *S. aureus* to be about 90% irrespective of the laser power. Thus, according to this embodiment, bacteria B can be collected and trapped alive at a high rate.

On the other hand, the collection density was dependent on the laser power with respect to any of *P. aeruginosa* and *S. aureus*. In this embodiment, in the case of the laser power of 0.04 W, a collection density was up (about $10^7$ Cells/cm$^2$). The maximum density is approximately 1000 times the density of the case without light irradiation. Thus, in order to achieve the highest possible collection densities, it is desirable to set the laser power to an appropriate value by experiment or simulation.

The reasons why a collection density of bacteria B drops as the laser power becomes higher than (104 W are considered as the following two points. The first reason is that the number of bacteria which can be trapped in each pore P has an upper limit. Therefore, when the number of bacteria trapped in the pores P in the vicinity of the laser spot reaches the upper limit and thus saturates, no more bacteria B are trapped even if the number of bacteria towards the laser spot is increased by growing convection with an increase in the laser power. The second reason is that as microbubbles MB grow with increasing laser power, as described above, the region where bacteria B can not enter is increased.

<Evaluation of the Function of Collected Bacteria>

From images explained in FIG. 14 and FIG. 15, it has been confirmed that there was no substantial damage to the cell membrane (the outer membrane) of bacteria B by laser beam irradiation L1. However, no damage to the cell membrane of the collected bacteria B does not necessarily mean that the bacterium B maintains its function. Therefore, by adding the honeycomb polymer film 12 after bacteria B were collected to a culture medium (liquid medium), the collected bacteria B were cultured.

Figure 19:
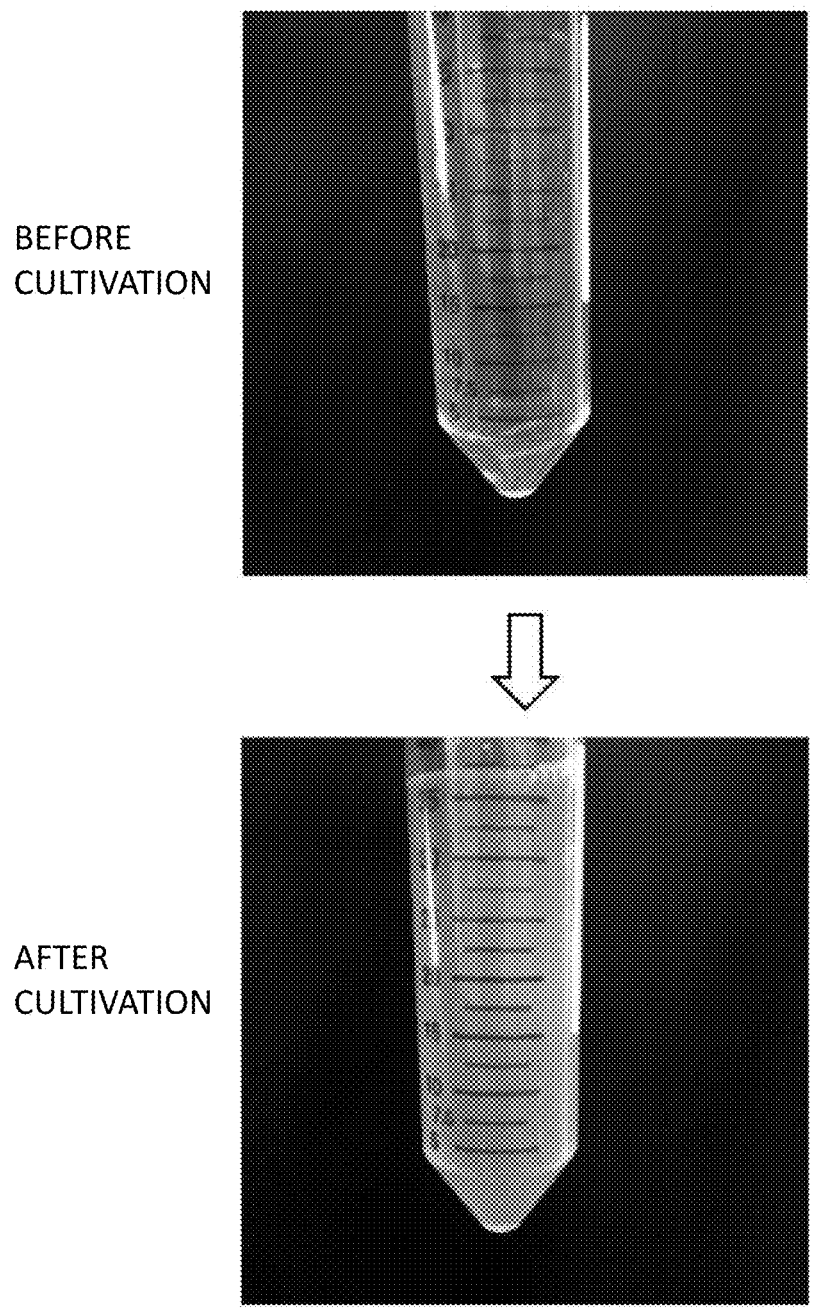
FIG. 19 is an image of the culture medium before and after culture of the collected bacteria.

FIG. 19 is an image of a culture solution before and after cultivation of the collected bacteria B. FIG. 19 (*a*) shows an image before the start of culture, FIG. 19 (*b*) shows the image after 18 hours of culture. Comparing the images of the culture medium before and after the culture, it was confirmed that the culture solution after culture was suspended as compared to the culture solution before incubation. This means that the collected bacteria B grew. Thus, it can be seen that bacteria B collected by collecting device 1 according to this embodiment maintain their function (metabolic function or growth function).

<Comparison with Comparative Examples>

Figure 20:
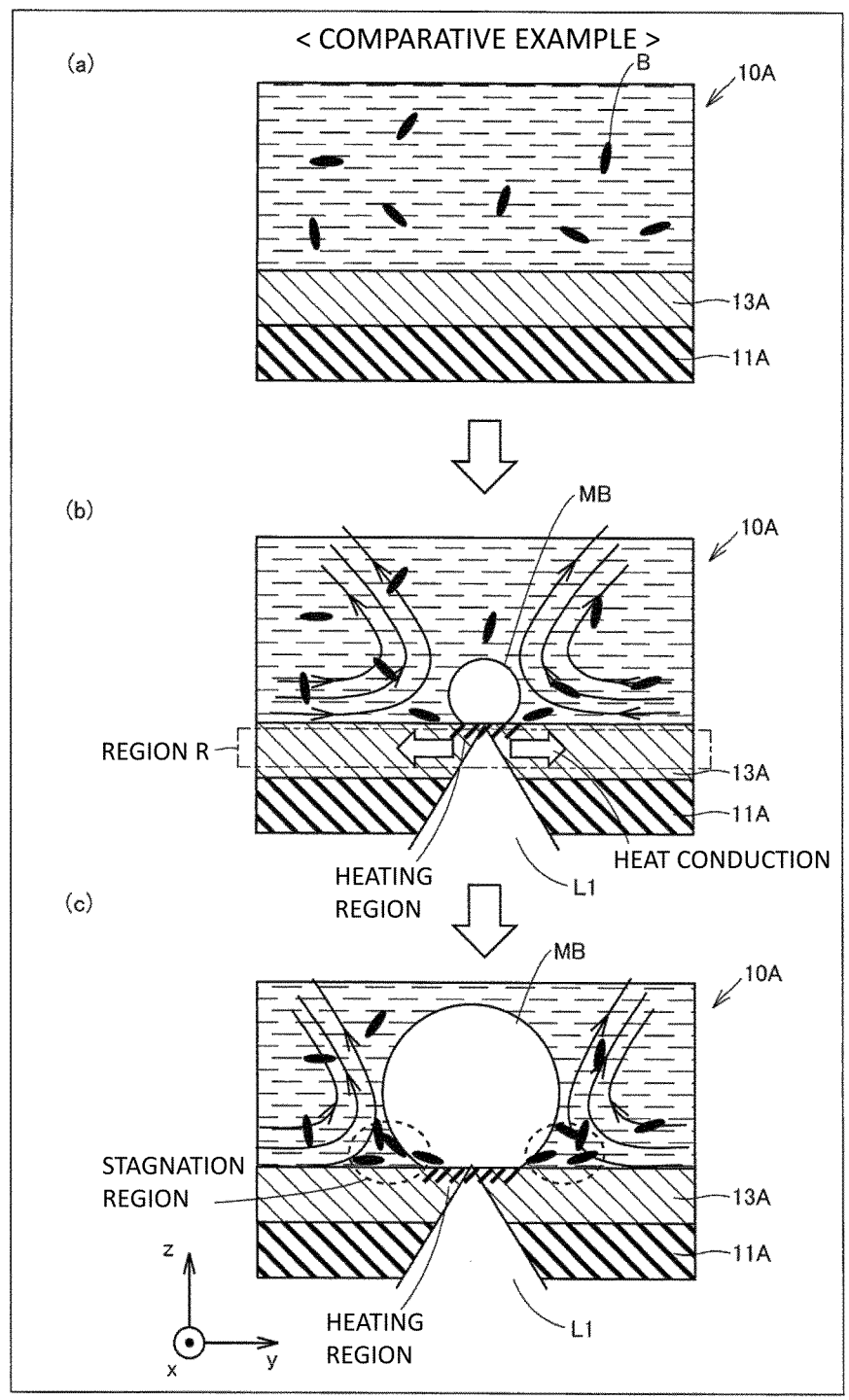
FIG. 20 is a diagram for explaining a bacterial collecting mechanism in Comparative Example.
Figure 21:
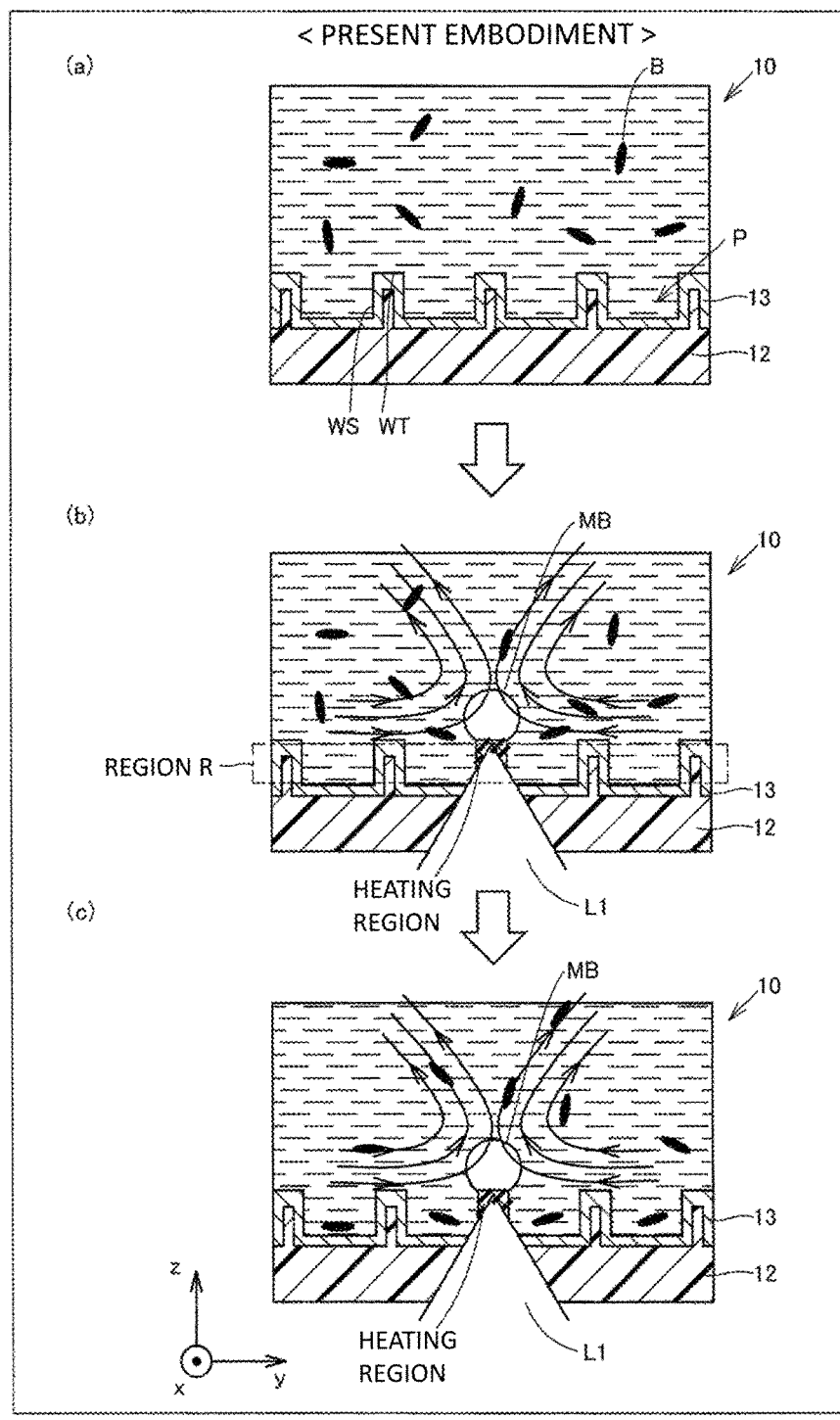
FIG. 21 is a diagram for explaining a bacterial collecting mechanism of the present embodiment in detail.

Hereinafter, the bacteria collecting mechanism according to the present embodiment will be described in detail while comparing with bacterial collecting mechanism according to a comparative example to help understanding (see international Publication WO2015/170758), FIG. 20 is a diagram for explaining a bacterial collecting mechanism in Comparative Example. FIG. 21 is a diagram for explaining a bacterial collecting mechanism of the present embodiment in detail. First, the difference in heating by photothermal effects will be described.

As shown in FIG. 20 (*a*), the collecting kit 10A according to the comparative example differs from the collecting kit 10 according to this embodiment in that it does not have honeycomb polymer film 12 formed on the substrate 11A. In collecting kit 10A, on a substrate 11A (e.g., cover glass), a thin film 13A of gold film on the order of nanometers in thickness is directly formed.

When the light irradiation is started, as shown in FIG. 20 (*b*), microbubbles MB is generated at the laser spot, and together therewith, convection occurs in the liquid. Microbubbles MB grows as temperature rises in the vicinity of the laser spot (see FIG. 20 (*c*)). Between the microbubbles MB and the thin film 13A, stagnation region arises in which the flow rate of the convection becomes substantially zero. In the comparative example, bacteria B carried by convection stay in the stagnation region (and the region surrounding it) and is thus collected.

Here, gold, or the material of the thin film 13A, is high in thermal conductivity as well as photothermal conversion efficiency. More specifically, the dispersion medium, or water, has thermal conductivity of 0.6 W/(m·K), and the thermal conductivity of the glass, which is the material of the substrate 11A, is 1 W/(m·K), the thermal conductivity of gold is 80 to 320 W/(m·K). The thermal conductivity of polystyrene, which is a substrate of honeycomb polymer film 12, is 0.1 W/(m·K). Note that these are all the thermal conductivity in the vicinity of room temperature (300 K). Further, as described in Bo Feng Zhixin Li, Xing Zhang "Prediction Of Size Effect On Thermal Conductivity Of Nanoscale Metallic Films", Thin Solid Films 517 (2009) 2803-2807, the thermal conductivity changes for a nano thin film.

When attention is focused on the area where highly thermally conductive gold thin film is formed (region f extending in the xy plane direction), in the comparative example, thin film 13A is formed along the surface of the substrate 11 Auniformly (continuously). As a portion of the thin film 13A where the laser beam L1 is irradiated is a heat source, heat generated by this heat source is conducted through the thin film 13A in the xy plane direction. Therefore, a relatively wide range of liquid is heated (showing a heating region by hatching). Therefore, in the stagnation region where bacteria Bis collected, the temperature of the thin film 13A may rise over a wide range. As a result, there is a possibility that the ratio of the killed bacteria B may increase.

In contrast, in the present embodiment, as shown in FIG. 21 (a), a honeycomb polymer film 12 is formed on a substrate 11, a thin film 13 is further formed on the honeycomb polymer film 12. Then, a portion of the thin film 13 formed on the surface of the partition wall W serves as a heat source. This heat source is projected into a liquid, and heat generated by the heat source heats the liquid near the heat source intensively. Furthermore, in the region of the partition wall W between the thin film 13 (the area between the side surface WS and another side surface WS in xy plane direction) is present polystyrene having low thermal conductivity. Heat conduction in the xy plane direction is also inhibited by polystyrene, and heat is easily trapped in the vicinity of the heat source in the xy plane direction. Accordingly, the area where the heat is conducted in the present embodiment (a heating region) is smaller than the heating region in the comparative example.

Thus, while a laser spot acts as a "plane heat source" in the comparative example, the laser spot in this embodiment is so to speak acts as a "point heat source." Therefore, in this embodiment, as compared with the comparative example, the range in which the temperature of the thin film 13 is excessively increased is narrowed, and the thermal damage to trapped bacteria Bin the pores P in a wide range around the laser spot is reduced. Therefore, it is possible to reduce the rate of killing bacteria B to improve the survival rate of the bacterium B.

Furthermore, in the present embodiment, the relative positional relationship between the collecting kit 10 and the objective lens 70 is adjusted to irradiate the thin film 13 formed on the partition wall W with the laser beam L1. The irradiation position of the laser beam L1 may be a side surface WS of the partition wall W, but more preferably, it is a top WT of the partition wall W.

It is conceivable to irradiate the laser beam L1 to the thin film 13 formed on the bottom PB of the pores P. Then, since the occurrence of convection is inhibited by the partition wall W, laser power must be sufficiently high to produce the convection. In contrast, in this embodiment, by irradiating the laser beam L1 to the partition wall W, it is possible to cause convection at relatively low laser power. As a result, it is possible to suppress an excessive temperature rise of the thin film 13, and the survival rate of the bacteria B can be further improved.

In general, the honeycomb structure is known to have water repellency (and oil repellency) caused by its structure. Furthermore, gold, which is the material of the thin film 13 is hydrophobic. Therefore, the dispersion medium of water hardly penetrates into the pores P, and air can be present in pores P before light irradiation. Therefore, to help water to enter the pores P, it is desirable to apply alcohol treatment to the surface of the substrate 11 before dropping the liquid onto the substrate 11 to alter the substrate 11 surface to be hydrophilic.

The following describes an effect to trap bacteria B by honeycomb polymer film 12, The honeycomb structure, while having water repellency (and oil repellency) as described above, has properties for holding liquid once the liquid has entered the pores (liquid retention). This is due to interfacial tension (more specifically, capillary force) at the interface between the liquid and pore surface. Bacteria B collected in the vicinity of the laser spot by convection and trapped in the pores P is retained with the liquid in the pores P by the liquid retaining property of the honeycomb structure. Therefore, it is possible even after stopping the light irradiation to trap bacteria B in the pores P. Note that the trapped bacteria B may be fixed to the inner wall or bottom of the pores P using an antibody or the like.

Thus, pore size of the upper limit value (upper limit size) is preferably determined in consideration of the size for which capillary forces (or capillary action) occurs. Whether the capillary phenomenon occurs remarkably is mainly determined by the surface tension of the liquid, and wettability of the pore surfaces with the contact angle as an index value, and the pore size. As in this embodiment, the main component of the liquid is water, and if metal thin film is formed on the pore surfaces formed of resin, the pore size of the upper limit value is preferably several 100 µm, more preferably several tens µm. The pore size of the lower limit (lower limit size) is determined according to the size and number of bacteria B (or other microscopic objects) to be collected. Pore size of the lower limit is greater than the minor axis of at least one bacteria B.

Similarly, the height (or depth) of the partition wall W of the pores P is also determined according to the size and number of bacteria B (or other microscopic objects). The upper limit of the height of the partition wall W is preferably several hundreds µm, more preferably 10 µm. The lower limit of the height of the partition wall W is preferably greater than the minor axis of the bacteria B, but it is not particularly limited as long as it can trap at least one bacteria B, and for example, it may be about half of minor axis of bacteria B.

As described above, according to this embodiment, irradiating the laser beam L1 to the thin film 13 as a photothermal conversion member formed on the honeycomb polymer film 12 causes convection by the optical heating effect. Since the honeycomb polymer film 12 has a plurality of pores P arranged in a honeycomb shape, it can collect the bacteria B at a high density, and furthermore, can trap the bacteria. Also, by generating convection, it is possible to promote the collecting of bacteria B in the vicinity of the laser spot to shorten the collecting time. Further, since the region in which excessive temperature rise by the heat confinement effect by the honeycomb structure occurs is narrowed, it is possible to trap bacteria B at a high survival rate. Further, the bacteria B trapped in the pores P by light irradiation can also be held trapped in the pores P by the liquid retaining property of the honeycomb structure even after stopping the light irradiation.

Modification of Embodiment

In the embodiment, as a space in which a plurality of bacteria B are trapped, a plurality of pores P which are arranged in a honeycomb shape is described as an example. However, construction of the "space for capturing a plurality of microscopic objects" according to the present invention is not limited thereto. In Modification 1-3 of the embodiment be described another example of a "space".

Figure 22:
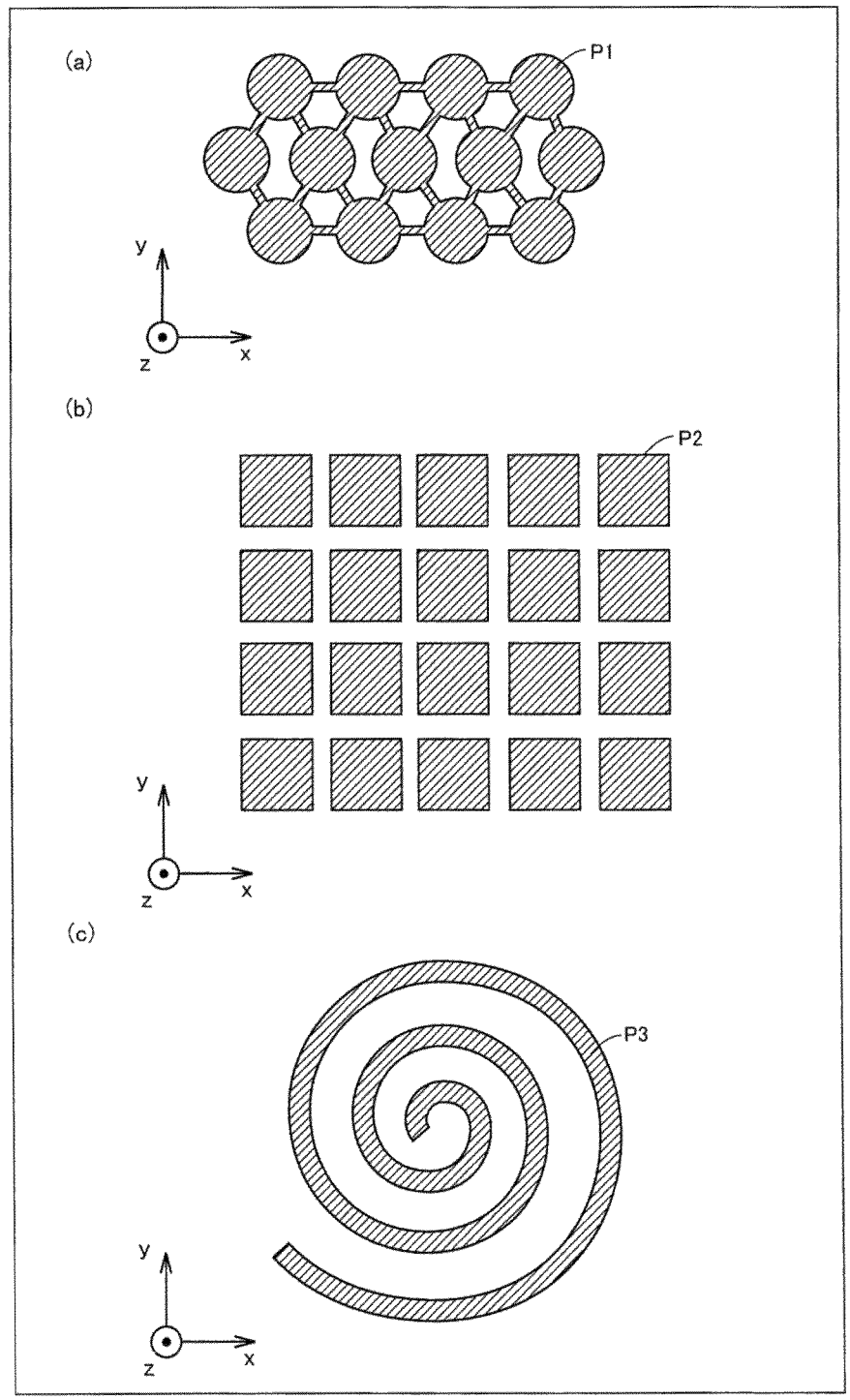
FIG. 22 is a top view of the collecting kit for explaining examples of the "space" for trapping microscopic objects according to a modification of the embodiment.

FIG. 22 is a top view of the collecting kit for explaining an example of a space for capturing the microscopic object according to a modification of the embodiment. In the sectional view shown in FIG. 5 (b), adjacent pores of the plurality of pores P communicate with each other at the bottom PB, However, as shown in FIG. 22 (a), a plurality of pore P1 may communicate with each other in the top surface (opening) of the plurality of pores.

The arrangement of the plurality of pores P is not limited to the honeycomb shape. Furthermore, the opening shape of each pore P is not limited to a circle. (ellipse). Any polygon having a size larger than the size of the microscopic object as the target of collecting can be arbitrarily arranged. For example, as shown in FIG. 22 (b), square pores P2 may be arranged in a matrix. However, by arranging a plurality of pores P, each having a circular opening shape in a honeycomb shape, it is possible to most densely arrange the pores.

Furthermore, one or more grooves may be formed instead of the plurality of pores P. The shape of the grooves is not particularly limited and may be, for example, concentric or linear FIG. 22 (c) shows a groove P3 of the vortex shape. Note that by using the micro-processing technology such as photolithography pores or grooves of a desired shape can be formed on a glass substrate or the like.

The embodiments disclosed herein are to be considered as not restrictive but illustrative in all respects. The scope of the invention is indicated by the appended claims rather than the description above, and is intended to include all modifications within the meaning and range of equivalency of the claims.

[Summary]

A collecting device for microscopic objects according an aspect of the present invention, collects the plurality of microscopic objects dispersed in a liquid. The collecting device includes a light source for emitting light, and a holding member which is capable of holding the liquid. In the holding member, an inner wall portion for defining a space, in which a plurality of microscopic objects dispersed in the liquid are trapped, is formed, and a photothermal conversion area for converting light from the light source into heat is formed. Photothermal conversion area converts the light from the light source to heat and thus heats the liquid to cause a convection in the liquid.

Preferably, the holding member has a plurality of pores formed as the space, and a partition wall separating adjacent pores of the plurality of pores from each other is formed as an inner wall portion and a photothermal conversion area. The collecting device further comprises an objective lens for focusing light from a light source, and an adjusting mechanism configured to irradiate, the light focused by the objective lens to the partition wall by adjusting the relative positional relationship between the partition wall and the objective lens.

Preferably the holding member has a plurality of pores formed as the space. Each of the plurality of pores has a size that can hold a part of the liquid within the pores by the interfacial tension at the interface between the pores and the liquid.

Preferably, the plurality of pores are arranged in a honeycomb shape.

A collecting kit for microscopic objects according to another aspect of the present invention is used in the collecting device for collecting a plurality of microscopic objects dispersed in a liquid by the light irradiation. The collecting kit comprises a support, and a holding member which is formed on a support and capable of holding the liquid. In the holding member, a photothermal conversion area including a material that converts light from a light source into heat is formed. The photothermal conversion area generates the heat for heating the liquid to cause a convection in the liquid by the light from the light source. In the holding member, an inner wall portion for defining a space, in which a plurality of microscopic objects dispersed in the liquid are trapped, is further formed.

Preferably, in the holding member, a plurality of pores are formed as the space. Each of the plurality of pores has a size that can hold a part of the liquid within the pores by the interfacial tension at the interface between the pores and the liquid.

Preferably, the plurality of pores are arranged in a honeycomb shape.

Furthermore, a collecting methods for microscopic objects according another aspect of the present invention collects a plurality of microscopic objects dispersed in a liquid. The collecting method comprises a step of providing a holding member. In the holding member, an inner wall portion for defining a space in which a plurality of microscopic objects dispersed in the liquid are trapped is formed, and a photothermal conversion area including a material which absorbs light and converts the light into heat is formed. The collecting method further comprises a step of causing a convection in the liquid by irradiating light having a wavelength included in the light absorption band of the photothermal conversion member in the photothermal conversion area.

Preferably, in the holding member, a plurality of pores are formed as the space, and partition walls separating adjacent pores of the plurality of pores from each other are formed as the inner wall portions and the photothermal conversion area. The step causing a convection comprises focusing light by the objective lens and irradiating the focused light to the partition wall.

The present invention can be utilized as a collecting device for collecting useful microorganisms (bacteria etc.) for human beings. Alternatively, according to the present invention, it is possible to realize a removing device for collecting and removing microorganisms harmful to the human body.

The invention claimed is:

1. A collecting device of microscopic objects for collecting a plurality of microscopic objects dispersed in a liquid, the collecting device comprising:
    a light source that emits light;
    an objective lens that focuses the light from the light source;
    a holding member configured to hold the liquid;
    an adjusting mechanism configured to adjust a relative positional relationship between the holding member and the objective lens, wherein:
    the holding member has:
    a plurality of pores in which the plurality of microscopic objects are trapped, and
    a plurality of partition walls that each separates adjacent pores of the plurality of pores, and
    at least a portion of the plurality of partition walls includes
        a photothermal conversion area, formed on a top surface thereof, including a material that converts the light from the light source into heat, the adjusting mechanism is configured to:
adjust the relative positional relationship so that the top surface of a selected area in the photothermal conversion area is irradiated with the light focused by the objective lens, and
maintain the positional relationship at least during irradiating the top surface with the light and heating the liquid, thereby generating a convection in the liquid.

2. The collecting device of microscopic objects according to claim 1, wherein:
a main component of the liquid is water,
the holding member has water repellency, and
a diameter of each of the plurality of pores is determined to have a liquid retention property that holds a part of the liquid in which the plurality of microscopic objects are dispersed, by interfacial tension at an interface between the pores and the liquid.

3. The collecting device of microscopic objects according to claim 1, wherein:
the plurality of pores are arranged in a honeycomb shape, and
adjacent pores of the plurality of pores are in communication with each other.

4. A collecting device of microscopic objects for collecting a plurality of microscopic objects dispersed in a liquid, the collecting device comprising:
a light source that emits light,
an objective lens that focuses the light from the light source;
a holding member configured to hold the liquid;
an adjusting mechanism configured to adjust a relative positional relationship between the holding member and the objective lens; and
a controller configured to control the adjusting mechanism, wherein:
the holding member includes:
a plurality of pores in which the plurality of microscopic objects are trapped, and
a plurality of partition walls that each separates adjacent pores of the plurality of pores, and
at least a portion of the plurality of partition walls includes a photothermal conversion area, formed on a top surface thereof, including a material that converts the light from the light source into heat,
the controller is configured to control the adjusting mechanism so that the top surface of a selected area in the photothermal conversion area is irradiated with the light focused by the objective lens, and
the top surface generates a convection in the liquid by heating the liquid.

5. A collecting kit of microscopic objects, used in a collecting device for collecting, by light irradiation, a plurality of microscopic objects dispersed in a liquid, the collecting kit comprising:
a support, and
a holding member formed on the support and configured to hold the liquid, wherein:

the holding member has a plurality of pores in which the plurality of microscopic objects are trapped, and a plurality of partition walls that each separates adjacent pores of the plurality of pores,
at least a portion of the plurality of partition walls includes a photothermal conversion area, formed on a top surface thereof, including a material that converts light into heat,
a photothermal conversion area is configured to generate heat for heating the liquid so that a convection is generated in the liquid, when a top surface of a selected area in the photothermal conversion area is irradiated with light focused with an objective lens, the light having a wavelength included in a light absorption band of the photothermal conversion area.

6. The collecting kit of microscopic objects according to claim 5, wherein:
a main component of the liquid is water,
the holding member has water repellency, and
an upper limit value of a diameter of each of the plurality of pores is determined to have a liquid retention property that holds a part of the liquid in which the plurality of microscopic objects are dispersed, by interfacial tension at an interface between the pores and the liquid.

7. A collecting kit of microscopic objects according to claim 5, wherein:
the plurality of pores are arranged in a honeycomb shape, and
adjacent pores of the plurality of pores are in communication with each other.

8. A collecting method of microscopic objects for collecting a plurality of microscopic objects dispersed in a liquid, comprising:
preparing a holding member having a plurality of pores in which the plurality of microscopic objects are trapped and a plurality of partition walls that each separates adjacent pores of the plurality of pores, at least a portion of the plurality of partition walls including a photothermal conversion area formed on a top surface thereof, the photothermal conversion area including a material that converts light into heat, and
generating a convection in the liquid by irradiating the top surface of a selected area in the photothermal conversion area with light having a wavelength included in a light absorption band of the photothermal conversion area.

9. A collecting method of microscopic objects according to claim 8, wherein:
a main component of the liquid is water,
the holding member has water repellency, and
a diameter of each of the plurality of pores is determined to have a liquid retention property that holds a part of the liquid in which the plurality of microscopic objects are dispersed, by interfacial tension at an interface between the pores and the liquid,
the collecting method further comprising performing alcohol treatment on the holding member.

* * * * *

UNITED STATES PATENT AND TRADEMARK OFFICE
CERTIFICATE OF CORRECTION

PATENT NO. : 11,561,160 B2
APPLICATION NO. : 16/301310
DATED : January 24, 2023
INVENTOR(S) : Shiho Tokonami et al.

It is certified that error appears in the above-identified patent and that said Letters Patent is hereby corrected as shown below:

On the Title Page

At item (71), Line 2, "Osaki (JP)" should be -- Osaka (JP) --.

At item (73), Line 2, "Osaki (JP)" should be -- Osaka (JP) --.

In the Claims

At Column 19, Line 28, "light," should be -- light; --.

At Column 20, Line 50, "repellency, and" should be -- repellency, --.

At Column 20, Line 55, "liquid," should be -- liquid, and --.

Signed and Sealed this
Seventh Day of November, 2023

Katherine Kelly Vidal
*Director of the United States Patent and Trademark Office*